(12) United States Patent
Chen et al.

(10) Patent No.: US 9,457,031 B2
(45) Date of Patent: Oct. 4, 2016

(54) ANTIBACTERIAL PROTEIN KINASE INHIBITORS

(71) Applicant: The Ohio State University, Columbus, OH (US)

(72) Inventors: Ching-Shih Chen, Upper Alrintgon, OH (US); Santosh Salunke, Columbus, OH (US); Larry Schlesinger, Powell, OH (US); Abul K. Azad, Powell, OH (US)

( * ) Notice: Subject to any disclaimer, the term of this patent is extended or adjusted under 35 U.S.C. 154(b) by 0 days.

(21) Appl. No.: 14/418,250

(22) PCT Filed: Jul. 30, 2013

(86) PCT No.: PCT/US2013/052706
§ 371 (c)(1),
(2) Date: Jan. 29, 2015

(87) PCT Pub. No.: WO2014/022382
PCT Pub. Date: Feb. 6, 2014

(65) Prior Publication Data
US 2015/0258100 A1    Sep. 17, 2015

Related U.S. Application Data

(60) Provisional application No. 61/677,251, filed on Jul. 30, 2012, provisional application No. 61/820,956, filed on May 8, 2013.

(51) Int. Cl.

| | | |
|---|---|---|
| *C07D 231/12* | (2006.01) |
| *A61K 31/5377* | (2006.01) |
| *A61K 45/06* | (2006.01) |
| *A61K 31/415* | (2006.01) |
| *A61K 31/4192* | (2006.01) |
| *A61K 31/4155* | (2006.01) |
| *A61K 31/4178* | (2006.01) |
| *A61K 31/422* | (2006.01) |
| *A61K 31/4439* | (2006.01) |
| *A61K 31/454* | (2006.01) |
| *A61K 31/4709* | (2006.01) |
| *A61K 31/496* | (2006.01) |
| *C07D 401/12* | (2006.01) |
| *C07D 401/14* | (2006.01) |
| *C07D 403/10* | (2006.01) |
| *C07D 403/12* | (2006.01) |
| *C07D 409/12* | (2006.01) |
| *C07D 409/14* | (2006.01) |
| *C07D 413/12* | (2006.01) |

(52) U.S. Cl.
CPC ......... *A61K 31/5377* (2013.01); *A61K 31/415* (2013.01); *A61K 31/4155* (2013.01); *A61K 31/4178* (2013.01); *A61K 31/4192* (2013.01); *A61K 31/422* (2013.01); *A61K 31/4439* (2013.01); *A61K 31/454* (2013.01); *A61K 31/4709* (2013.01); *A61K 31/496* (2013.01); *A61K 45/06* (2013.01); *C07D 231/12* (2013.01); *C07D 401/12* (2013.01); *C07D 401/14* (2013.01); *C07D 403/10* (2013.01); *C07D 403/12* (2013.01); *C07D 409/12* (2013.01); *C07D 409/14* (2013.01); *C07D 413/12* (2013.01)

(58) Field of Classification Search
None
See application file for complete search history.

(56) References Cited

U.S. PATENT DOCUMENTS 6,506,747 B1 * 1/2003 Betageri .............. C07D 231/14
514/228.8

* cited by examiner

*Primary Examiner* — Samantha Shterengarts
(74) *Attorney, Agent, or Firm* — Tarolli, Sundheim, Covell & Tummino LLP

(57) ABSTRACT

Methods of treating bacterial infection by in a subject by administering a pharmaceutical composition including a celecoxib derivative are described. The compounds are particularly useful for treating infection by bacteria capable of growing inside macrophages, such as *Myocobacteria tuberculosis*.

2 Claims, 7 Drawing Sheets

ANTIBACTERIAL PROTEIN KINASE INHIBITORS

This application is the U.S. national phase entry of PCT/US2013/052706, with an international filing date of Jul. 30, 2013, which claims priority to U.S. Provisional Patent Application Ser. No. 61/677,251, filed Jul. 30, 2012, and U.S. Provisional Patent Application Ser. No. 61/820,956, filed May 8, 2013, all of which are incorporated herein by reference.

BACKGROUND

*Tuberculosis* (TB) and problems associated with its treatment. TB is one of the leading human infectious diseases caused by the bacterium *Mycobacterium tuberculosis* (M. tb). It remains a major world-wide public health problem and continues to pose a serious threat to the global population, especially in third-world countries. According to the WHO, TB incidence and prevalence were estimated to be 8.8 and 12 million cases respectively, in 2010. 1.45 million, which includes 1.1 million among HIV-negative and 0.35 million among HIV-positive, people died from TB in the same year. *Tuberculosis* and HIV co-infection is one of the current major challenges in the control of TB, since HTV infection increases the risk of developing active TB. Most importantly, one-third of the world population has latent TB infection and 10% of those infected people will develop active TB at some point during their life time. Furthermore, multi drug-resistant (MOR) TB has become increasingly prevalent, and extremely drug-resistant (XOR) and totally drug-resistant (TOR) forms of TB are also emerging posing a major threat to progress in global TB control. Only 1% of patients with MOR-TB are estimated to be on appropriate drug treatment, with predicted poor treatment outcomes. The existence of chronic diseases such as diabetes is known to increase the risk of developing active TB by 3-fold. All of these situations together highlight an urgent need of new drugs with novel mechanisms of action, especially for the effective management of MOOR—, XOR— and TOR TB.

The focus of anti-TB drug development has always been on regimens rather than on single drugs to reduce the risk of development of resistance given the duration of therapy. Such regimens should include new drugs with novel mechanisms of action that do not demonstrate cross-resistance to current first- and second line TB drugs. An ideal drug combination should consist of at least three drugs that are bactericidal against both susceptible and resistant strains of M. tb, and have potent, complementary and synergistic activities against various subpopulations of M. tb (notably persisters). This combination should produce a stable cure in a much shorter period of time than the current prolonged treatment of 6 months to 2 years. Additionally, such a novel combination should be useful for the treatment of patients with M. tb and HIV co-infection such that the drug interactions with antiretroviral drugs are limited avoiding the current removal of rifampicin from the regimen. However, the need for multiple drugs taken simultaneously and for a long duration can cause toxicity and result in poor patient compliance.

Apart from nearly-approved drugs (or drugs at the final stage of clinical development) such as gatifloxacin, moxifloxacin and linezolid, there are approximately 11 compounds in different phases of clinical trials for TB. They are: PA-824 (a nitroimidazole), OPC-67683 (a nitroimidazole), PNU-100480 (an oxazolidinone), AZD5847 (an oxazolidinone), SQ609 (a diamine derivative), SQ109 (a diamine derivative), DC-159a (a fluoroquinolone), TMC207 (a diarylquinoline), BTZ043 (a nitrophenyl derivative), DNB 1 (a nitrophenyl derivative), and BDM31343 (an oxadiazole derivative). New targets of some of them have also been identified. Of note, the most promising anti-TB drug compound, TMC207, was found to be a mycobacterial ATP synthase inhibitor, and this target was found using the approaches described in this proposal. Thus, strategies for the development of new anti-TB drugs are ready to fuel the existing pipeline of TB drug regimens. However, despite progress so far, the global drug TB pipeline is still grossly insufficient to address unmet treatment needs, particularly with regard to providing novel, short course, and safe drugs that are effective against drug resistant TB.

Drug screening procedures. Recent advances in biochemistry and genetics have offered screening of drug molecules by a target-based approach. However, this approach has had little success in the anti-bacterial drug discovery area in general. The essential nature of a target for bacterial replication may be a prerequisite but it does not ensure its druggability; for many essential targets it has not been possible to identify specific inhibitors with drug-like properties. For example, several high-throughput screening projects for identifying inhibitors of isocitrate lyase, a key glyoxylate-shunt-pathway enzyme found to be essential for mycobacterial intracellular growth and their long-term persistence in mice, were discontinued due to the lack of druggability of this target. Although not absolutely free of drawbacks, whole bacterial cell-based phenotypic screening approaches have been proven to be a more successful strategy for identifying new drug candidates. Such a strategy recognizes the potential holistic interactions of a drug target(s) with one or more components in a bacterial cell and defines its essentiality in a more physiologically relevant manner. One of the recent successes with the whole cell-screening approach has been the identification of the potent new TB drug candidate diarylquinoline (TMC207).

Screening for anti-TB drugs should not be limited to compound libraries based solely on anti-bacterial targets, but rather should be extended to other classes of libraries based on eukaryotic or mammalian targets for the creation of successful drug regimens. For example, two anti-psychotic drug molecules phenothiazine and diarylquinoline (TMC207) have been shown to possess potent anti-TB activities upon re-purposed screening. A bicyclic nitroimidazofuran compound, PA-824, which had been investigated as a potential radio-sensitizing agent for use in cancer radiotherapy, was later found to display anti-TB activities in both in vitro and in vivo models. While some need TB drug candidates are being identified, there still remains a need for the identification of additional drugs for use in treating this difficult to treat disease.

SUMMARY OF THE INVENTION

The inventors investigated the potential of mammalian target-directed small molecules as anti-bacterial agents. It is now estimated that about 20-30% of drug candidates, in general, currently under clinical development are protein kinase inhibitors. OSU-03012 is a protein kinase inhibitor and a potential anti-cancer drug candidate. A collection of related small molecules with distinct scaffolds have been prepared and screened for their activity using a newly developed in vitro bioluminescence assay. The whole cell phenotypic screening approach has also been used to help identify drug candidates.

A method of treating bacterial infection in a subject is described herein that includes administering to the subject a therapeutically effective amount of a compound of formula I or formula II or a pharmaceutically acceptable salt thereof:

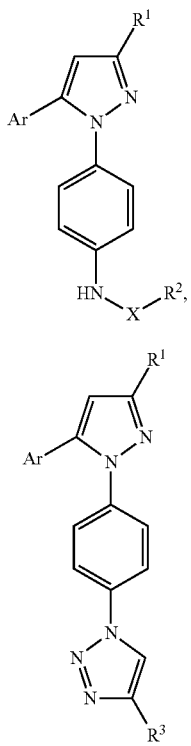

wherein $R^1$ is selected from —$CF_3$, —$NH_2$, —$CO_2H$, —$CO_2Me$, —$CONH_2$, —$CONHNH_2$, —$CONHMe$, —CO-piperazine, —CO-pyrrolidine, —CONH-glycine, —$CH_2CH_2CO_2Me$, —$CH_2CH_2CONH$—$C_1$-$C_4$ alkyl, —NHCO—$C_1$-$C_4$ alkyl, —$NHSO_2NH_2$, —$NHSO_2N(Me)_2$, —NHCONH—$C_1$-$C_4$ alkyl, —$NHCONH_2$, —$NHCO_2$—$C_1$-$C_4$ alkyl; Ar is a substituted or unsubstituted phenyl, biphenyl, naphthalenyl, or anthracenyl group; X is C=O or O=S=O, $R^2$ is a substituted or unsubstituted cycloalkyl, heterocycloalkyl, aryl, or heteroaryl group, and $R^3$ is H, $CH_2OH$, acetyl, $C_1$-$C_4$ alkyl, alkylamine, cycloalkyl, heterocycloalkyl, $C_1$-$C_4$ alkyl ether, $C_1$-$C_4$ alkyl ester, $C_1$-$C_4$ alkyl amide, or methylsulfonamidomethyl, or a pharmaceutically acceptable salt thereof.

In some embodiments, the bacterial infection is infection by bacteria capable of growing inside a macrophage. In another embodiment, the bacteria are of the genus *mycobacterium*. The method can also be useful for treating multidrug resistant *tuberculosis*.

DETAILED DESCRIPTION OF THE INVENTION

Definitions

Figure 1:
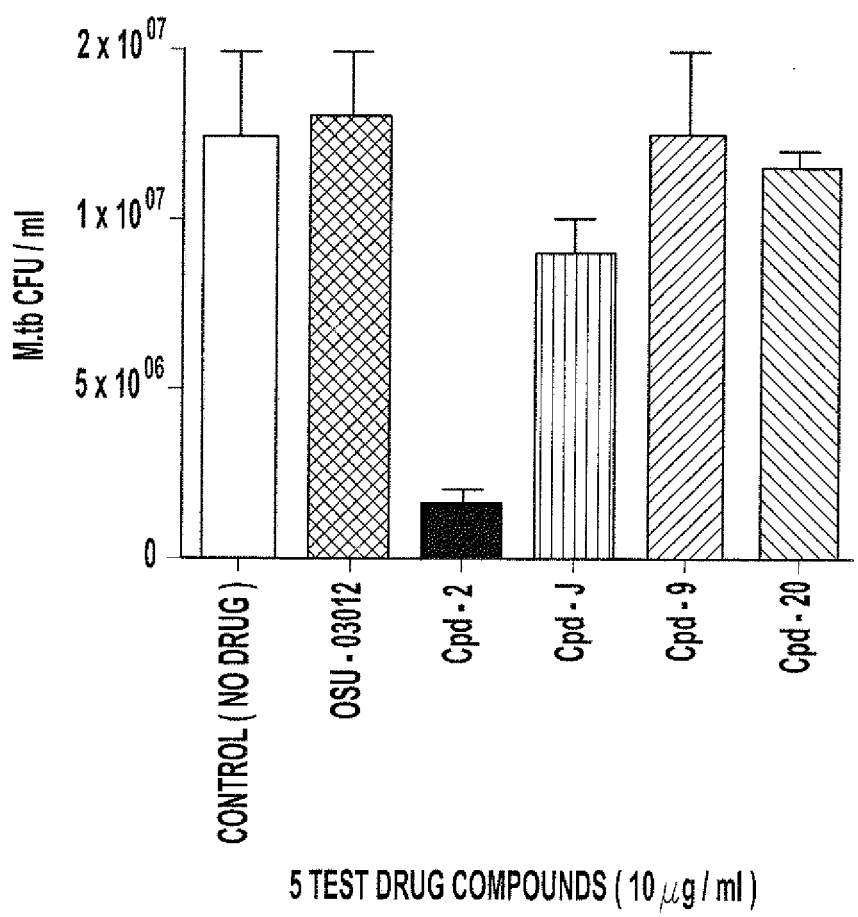
FIG. 1 provides a bar graph showing the antimycobacterial activity of OSU-03012-related derivatives.
Figure 2:
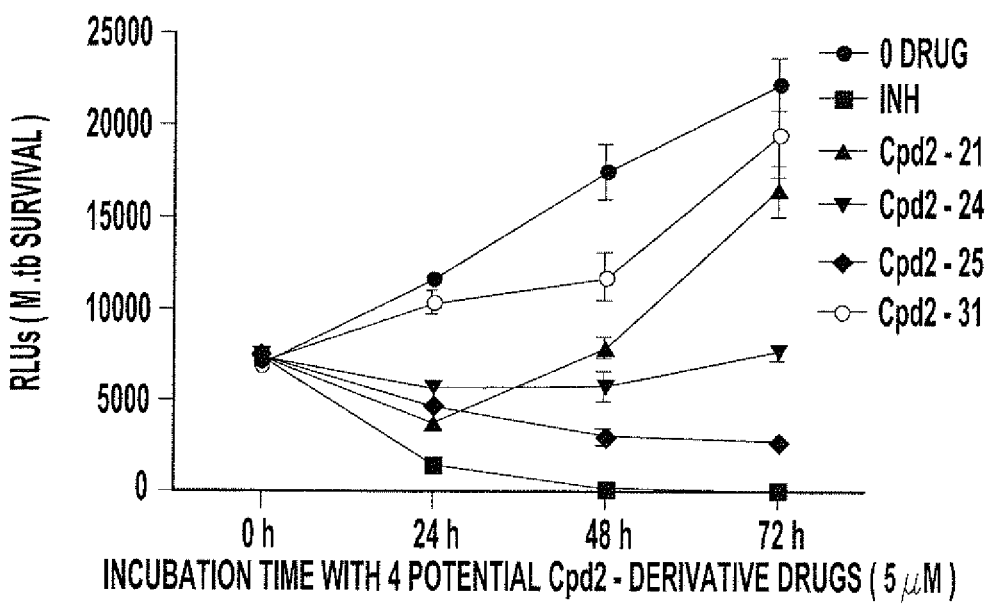
FIG. 2 provides a line graph showing the antimycobacterial activity of first generation compounds derived from Cpd 2 as evaluated by the bacterial luminescence assay.
Figure 3A:
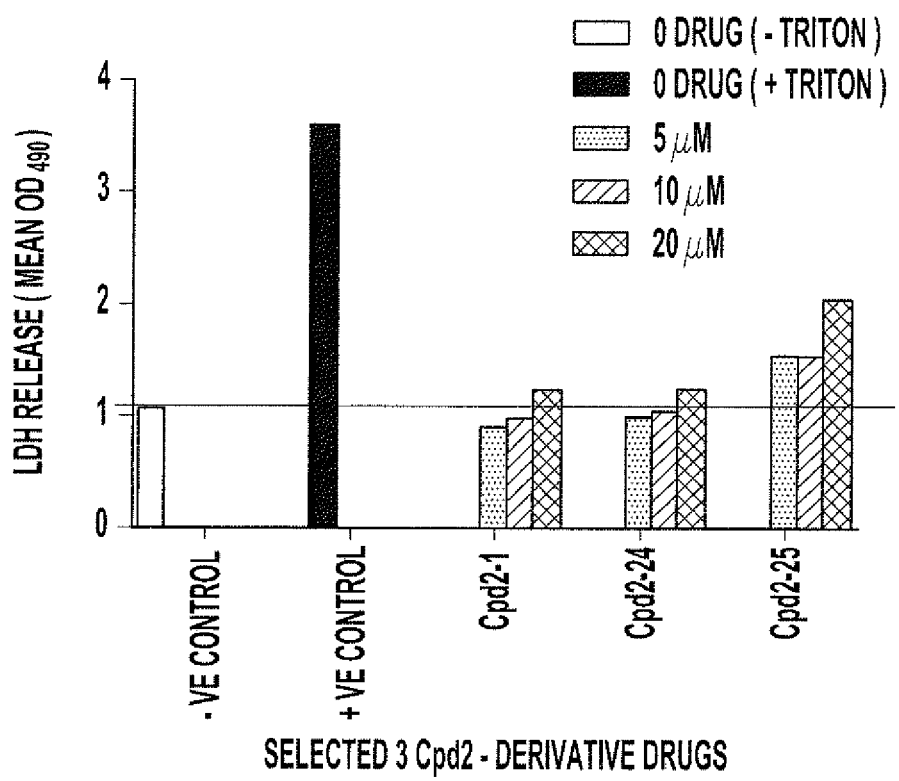
FIG. 3a provides a bar graph showing the decreased toxicity of Cpd-24 and 3b provides a line graph showing its higher ability to inhibit intramacrophage M. tb growth.
Figure 3B:
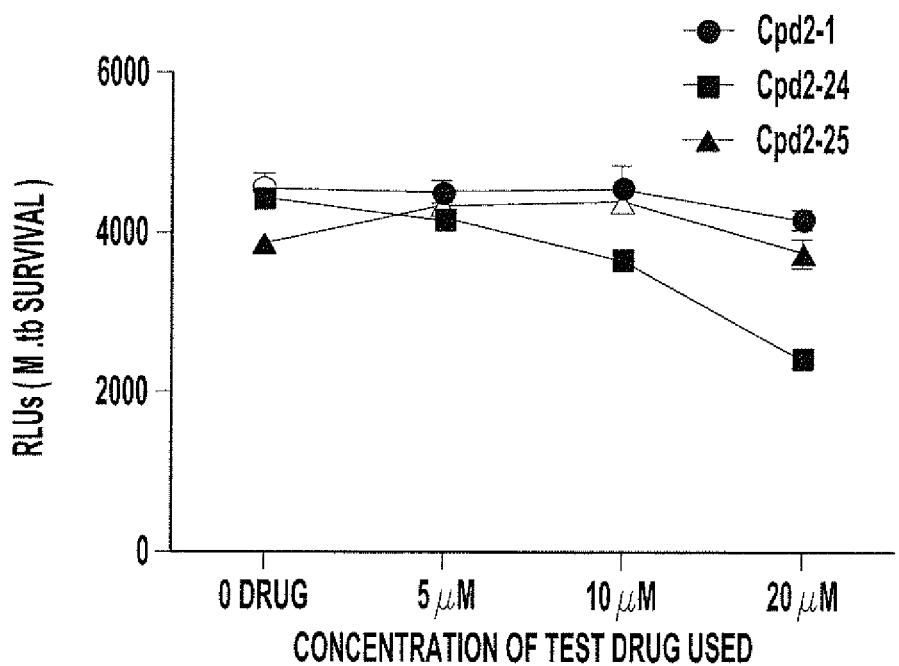
Figure 4A:
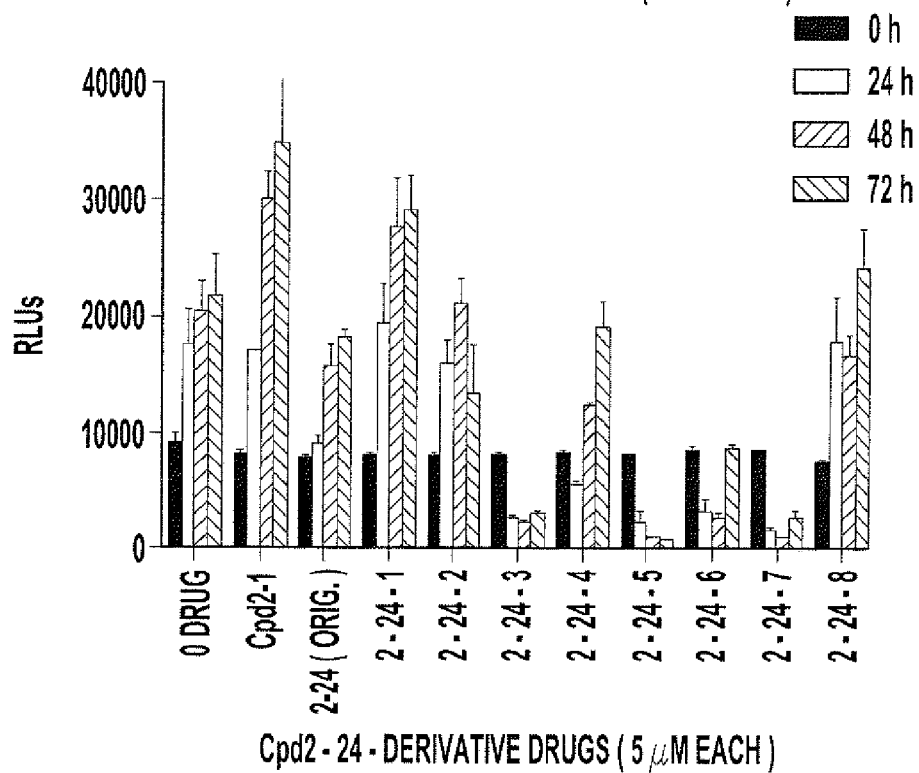
FIG. 4 provides graphs showing the in vitro antimycobacterial activity of cpd2-24-derivative compounds cpd2-24-1 through cpd2-24-8 at 5 µM concentration against M. tb during 72 h time period (4a, all 8 compounds; 4b, 4 selected potent compounds).
Figure 4B:
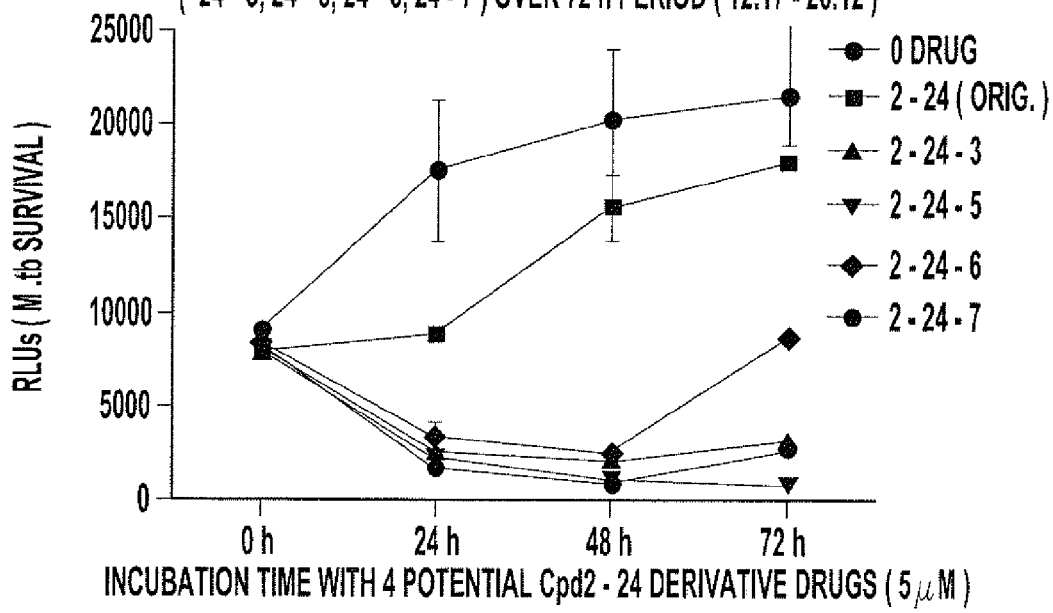
Figure 5A:
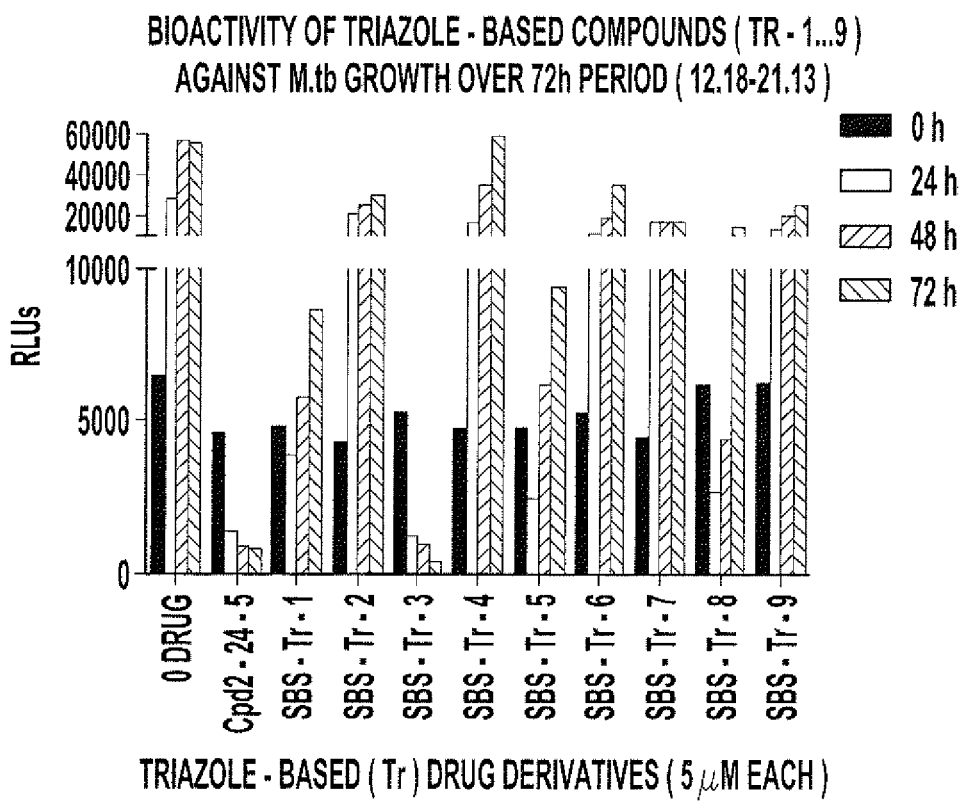
FIG. 5 provides graphs showing the in vitro antimycobacterial activity of triazole-based derivative compounds SBS-Tr-1 through SBS-Tr-9 at 5 µM concentration against M. tb during 72 h time period (5a, all 9 compounds; 5b, 3 selected potent compounds plus cpd2-24-5).
Figure 5B:
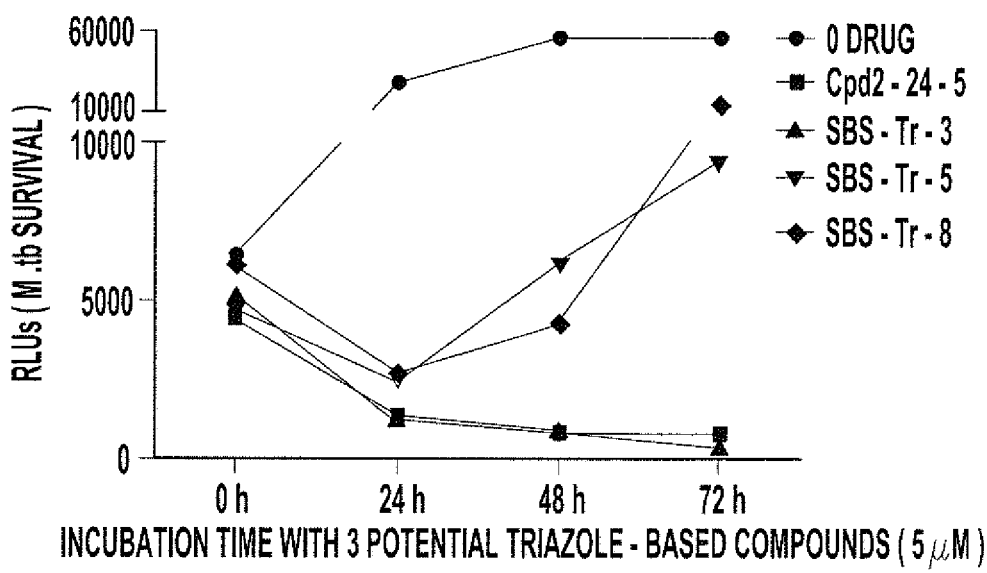
Figure 6A:
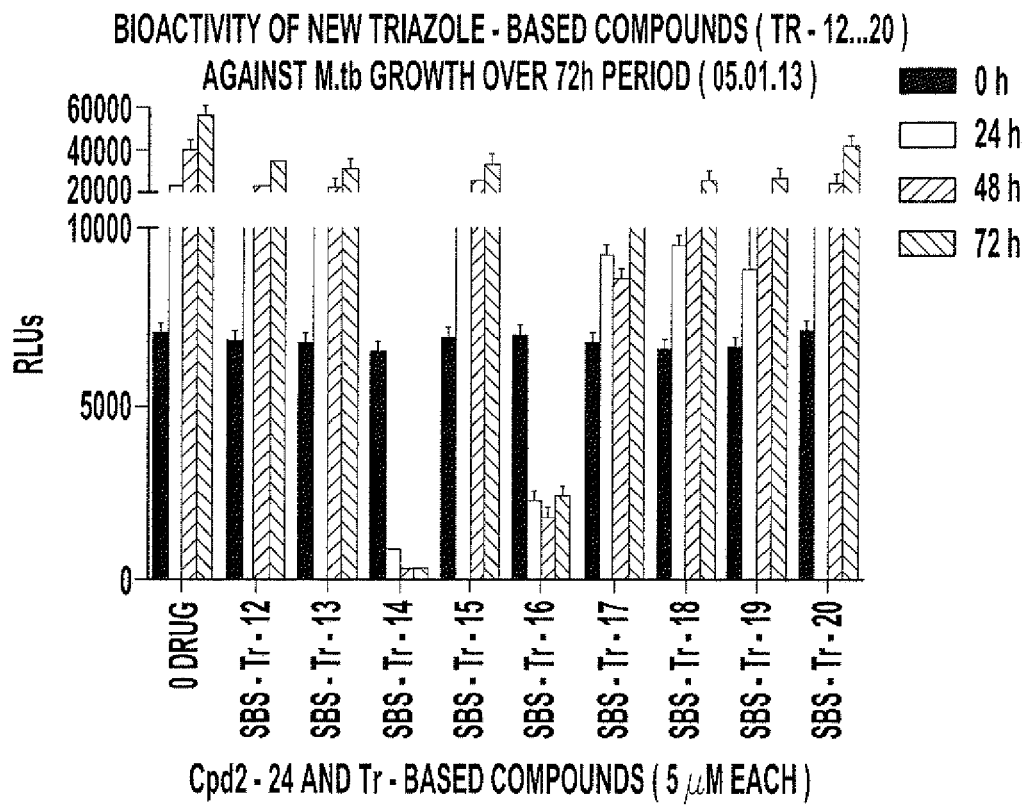
FIG. 6 provides graphs showing the in vitro antimycobacterial activity of additional cpd2-24-derived and triazole-based derivative compounds at 5 µM concentration against M. tb during 72 h time period, with 6a showing the bioactivity of new Tr-based compounds Tr-12 through Tr-20 and 6b showing M. tb growth inhibition by 4 additional new compounds.
Figure 6B:
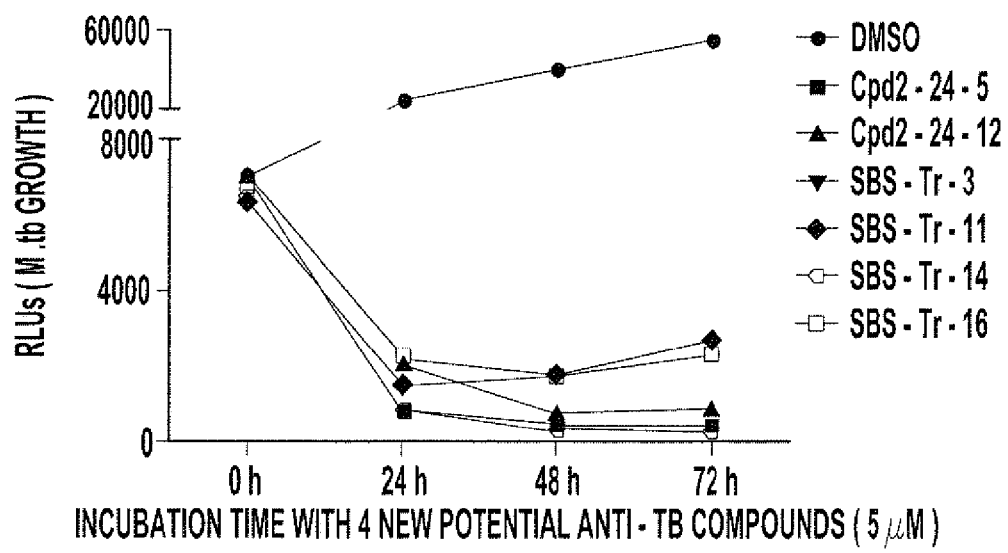
Figure 7A:
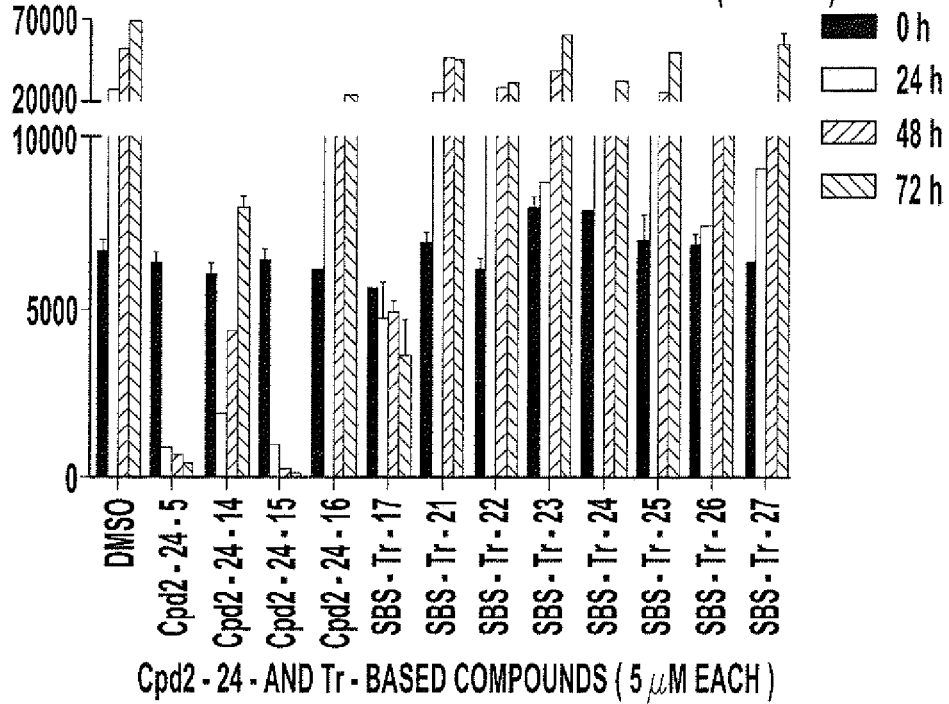
FIG. 7 provides graphs showing the in vitro antimycobacterial activity of further cpd2-24-derived and triazole-based derivative compounds at 5 µM concentration against M. tb during 72 h time period, with 7a showing the bioactivity of cpd2-24-14-16, Tr-17, and Tr-based compounds Tr-21 through Tr-27 and 6b showing M. tb growth inhibition by 3 additional new compounds as compared to a DMSO control.
Figure 7B:
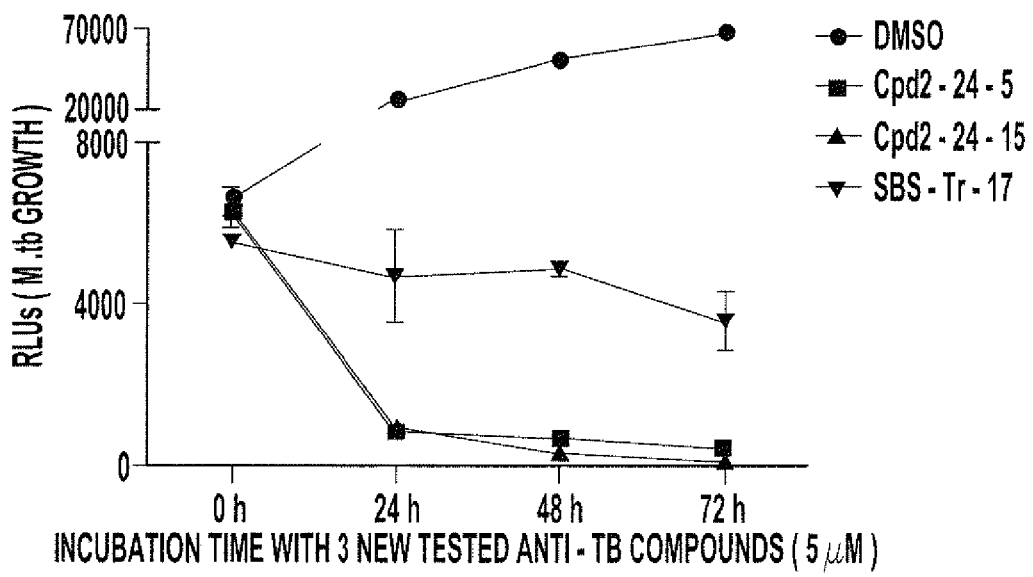

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for celecoxib derivatives of this invention are those that do not interfere with the antibacterial activity of the celecoxib derivatives. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocycloalkyl" refers to non-aromatic rings including at least one ring heteroatom. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl groups. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as ($C_1$-$C_6$) heterocycloalkyl.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Additional substituents that can optionally be substituted on a group are further defined below.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CHO$_2$.

Amino: —NR$^1$R$^2$, wherein R$^1$ and R$^2$ are independently amino substituents, for example, hydrogen or a $C_{1-7}$ alkyl group. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino.

Acylamido (acylamino): —NR$^1$C(=O)R$^2$, wherein R$^1$ is an amide substituent, for example, hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. Acylamido groups can be substituted; for example, the acylamido groups can be amine substituted acylamido groups having the formula —NH—CO—(CH$_2$)$_x$—NH$_2$, wherein x is an integer from 1-4.

Ureido: —N(R$^1$)CONR$^2$R$^3$ wherein R$^2$ and R$^3$ are independently amino substituents, as defined for amino groups, and R$^1$ is a ureido substituent, for example, hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHC(=O)NHPh.

Sulfonyl (sulfone): —S(=O)$_2$R, wherein R is a sulfone substituent, for example, a $C_{1-7}$ alkyl group or a $C_{5-20}$ aryl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl). The sulfone substituent may in some cases be an amino group, as defined above. These groups may be termed "aminosulfonyl" groups.

Sulfonamino: —NR$^1$S(=O)$_2$R, wherein R$^1$ is an amino substituent, as defined for amino groups, and R is a sulfonamino substituent, for example, a $C_{1-7}$ alkyl group or a $C_{5-20}$ aryl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Treat", "treating", and "treatment", etc., as used herein, refer to any action providing a benefit to a subject afflicted with a condition or disease such as a *Tuberculosis* infection, including improvement in the condition through lessening or suppression of at least one symptom, delay in progression of the disease, prevention or delay in the onset of the disease, etc.

Prevention, as used herein, refers to any action providing a benefit to a subject at risk of being afflicted with a condition or disease such as *Tuberculosis* infection, including avoidance of infection or a decrease of one or more symptoms of the disease should infection occur.

Macrophage cells, as used herein, refer to immune cells of the innate immune system, and include macrophages, macrophage-like cells, and macrophage precursors such as monocytes. Macrophage-like cells include tingible body macrophages, dendritic cells, foam cells, and multinucleated giant cells.

Multidrug resistance, as defined herein, is a condition enabling disease-causing bacteria to resist antibiotics, and can arise as a result of spontaneous mutation or by DNA transfer. Multidrug resistance enables some bacteria to oppose the action of certain antibiotics, rendering them ineffective. Several mechanisms can be used to provide multi-drug resistance, including no longer relying on a glycoprotein cell wall, enzymatic deactivation of antibiotics, decreased cell wall permeability to antibiotics, altered target sites of antibiotic, efflux mechanisms to remove antibiotics, and increased mutation rate as a stress response. Many different bacteria now exhibit multi-drug resistance, including staphylococci, enterococci, gonococci, streptococci, *salmonella*, as well as numerous other gram negative bacteria and *Mycobacterium tuberculosis*.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

Treatment of *Tuberculosis* Using Celecoxib Derivatives

In one aspect, the invention provides a method of treating bacterial infection in a subject. The method includes administering to the subject a therapeutically effective amount of a compound of formula I or formula II (referred to herein as Celecoxib derivatives) or a pharmaceutically acceptable salt thereof:

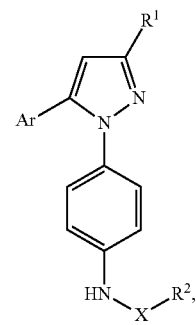

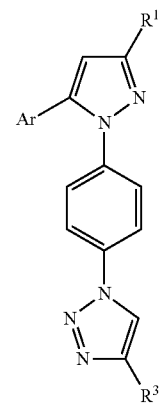

wherein $R^1$ is selected from —$CF_3$, —$NH_2$, —$CO_2H$, —$CO_2Me$, —$CONH_2$, —$CONHNH_2$, —CONHMe, —CO-piperazine, —CO-pyrrolidine, —CONH-glycine, —$CH_2CH_2CO_2Me$, —$CH_2CH_2CONH$—$C_1$-$C_4$ alkyl, —NHCO—$C_1$-$C_4$ alkyl, —$NHSO_2NH_2$, —$NHSO_2N(Me)_2$, —NHCONH—$C_1$-$C_4$ alkyl, —$NHCONH_2$, —$NHCO_2$—$C_1$-$C_4$ alkyl; Ar is a substituted or unsubstituted phenyl, biphenyl, naphthalenyl, or anthracenyl group; X is C=O or O=S=O, $R^2$ is a substituted or unsubstituted cycloalkyl, heterocycloalkyl, aryl, or heteroaryl group, and $R^3$ is H, $CH_2OH$, acetyl, $C_1$-$C_4$ alkyl, alkylamine, cycloalkyl, heterocycloalkyl, $C_1$-$C_4$ alkyl ether, $C_1$-$C_4$ alkyl ester, $C_1$-$C_4$ alkyl amide, or methylsulfonamidomethyl, or a pharmaceutically acceptable salt thereof.

Certain embodiments of the invention are directed to a particular subset of the celecoxib derivatives. Various embodiments can be directed to any subset of compounds encompassed by formulas I and II described herein. In some embodiments, the celecoxib derivatives include only compounds according to formula I, while in other embodiments the celecoxib derivatives include only compounds according to formula II.

In other embodiments, the substituents selected for the formula can be selected from a more limited group, either for formula I or formula II, or for both. In some embodiments, $R^1$ is —$CH_2CH_2CONH$—$C_1$-$C_4$ alkyl group, while in further embodiments $R^1$ is —$CH_2CH_2CONH$-Me (methylpropanamide). In other embodiments, Ar is a biphenyl group, while in further embodiments Ar is 4'-trifluoromethyl biphenyl. In further embodiments, Ar is 4'-trifluoromethyl biphenyl and $R^1$ is methylpropanamide.

In some embodiments of a compound according to formula I, X is C=O, while in other embodiments $R^2$ is a heteroaryl group. In a further embodiment, X is C=O and $R^2$ is a heteroaryl group. In yet further embodiments, $R^2$ is a phenylamide group. In a preferred embodiment, the compound has the formula:

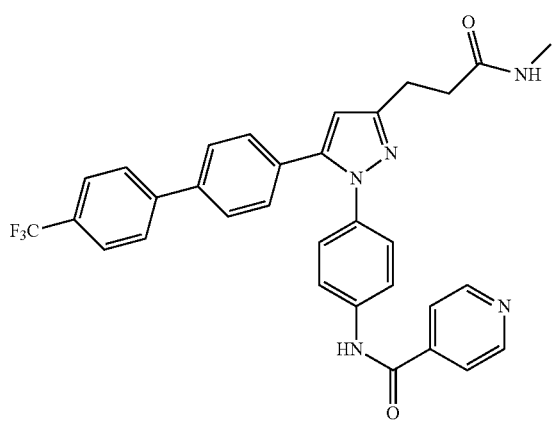 [SMILES: CNC(=O)CCc1cc(-c2ccc(-c3ccc(C(F)(F)F)cc3)cc2)n(-c2ccc(NC(=O)c3ccncc3)cc2)n1]

In some embodiments of a compound according to formula II, $R^3$ is selected from the group consisting of methyl alcohol (—CH$_2$OH), alkyl, and alkylamine groups. In a further embodiment, $R_3$ is a $C_1$-$C_4$ alkyl group or a $C_1$-$C_4$ alkylamine group. In a preferred embodiment, the compound has the formula:

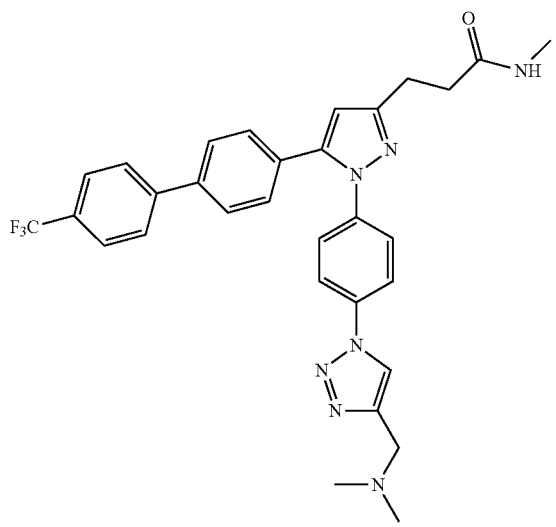

In some embodiments, the celecoxib derivatives are used to treat or prevent a bacterial infection by bacteria capable of growing inside macrophages. Examples of bacterial capable of intracellular growth include *Salmonella, Neisseria, Brucella, Mycobacterium, Listeria, Francisella, Legionella*, and *Yersinia pestis*. Due to cell membrane barriers, antibiotic treatment can be ineffective against intracellular bacteria, since most antibiotics are unable to penetrate the cell membrane or will be excluded by host cells. Even if an antibiotic can enter infected cells, intracellular bacterial growth might cause a transient antibiotic-resistance, causing a need of higher doses of antibiotics kill the intracellular bacteria.

A preferred bacteria for treatment by the celecoxib derivatives of the invention are bacteria of the genus *Mycobacterium*, which are the cause for a variety of diseases, including *tuberculosis*. A subset of *Mycobacterium* are bacteria characterized as being *mycobacterium tuberculosis* complex (MTBC) members, which are the causative agents of human and animal *tuberculosis*. Species in this complex include: *M. tuberculosis*, the major cause of human *tuberculosis, M. bovis, M. africanum, M. canetti, M. caprae, M. microti*, and *M. pinmpedii*.

Other species of Mycobacteria include *M. asiaticum, M. gordonae, M. gastri, M. kansasii, M. hiberniae, M. nonchromogenicum, M. terrae, M. trivial, M. ulcerans, M. pseudoshottsii, M. shottsii, Mycobacterium simiae clade, M. triplex, M. genavense, M. florentinum, M. lentiflavum, M. palustre, M. kubicae, M. parascrofulaceum, M. heidelbergense, M. interjectum, M. simiae, M. branderi, M. cookie, M. celaturn, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. locus, M. marinum, M. monacense, M. montefiorense, M. murale, M. nebraskense, M. saskatchewanense, M. scrofulaceum, M. shimoidei, M. tusciae*, and *M. xenopi*.

In some embodiments, the *tuberculosis* infection is inhibited in macrophage cells, which are the primary in vivo target for *tuberculosis*. As shown in the examples provided herein, celecoxib derivatives are able to effectively inhibit *tuberculosis* in macrophages. In additional embodiments, the celecoxib derivatives are able to inhibit *tuberculosis* in macrophages without significant toxicity to other cells, and macrophage cells in particular.

The celecoxib derivatives can also be administered to subjects to treat or prevent infection by multidrug resistant strains of *tuberculosis*. Multi-drug-resistant *tuberculosis* (MDR-TB) is defined as *tuberculosis* that is resistant to at least isoniazid and rifampicin. Celecoxib derivatives have been shown inhibitory activity against a number of mammalian enzymes, including phosphoinositide-dependent kinase-1, carbonic anhydrase, sarcoplasmic/ER calcium ATPase, and COX-1. Multidrug resistance can develop through various mechanisms, such as drug inactivation or modification, alteration of target site, or alteration of a metabolic pathway affected by an antibiotic. Accordingly, providing treatment with compounds having a different structure and different target sites, as exhibited by the celecoxib derivatives described herein, can circumvent existing multidrug resistance in many situations.

The celecoxib derivatives of formula I and II can also by administered together with an additional antituberculosis agent. In some embodiments, administration of the celecoxib derivative can provide synergistic results when administered together with an additional antituberculosis agent. Examples of antituberculosis agents include first line drugs such as isoniazid, rifampin, pyrazinamide, and ethanbutol, and second line drugs such as amikacin, kanamycin, capreomycin, biomycin, enviomycin, ciprofloxacin, levofloxacin, moxifloxacin, ethionamide, prothionamide, closerin, and terizidone. Second line drugs are generally used for treatment of multidrug resistant *tuberculosis*.

Celecoxib derivatives of the invention can be used for treatment by administering a therapeutically effective amount of the celecoxib derivative together with a pharmaceutical carrier to a subject that is already infected by *Tuberculosis*. In one embodiment of therapeutic administration, administration of the celecoxib derivatives is effective to eliminate the infection; in another embodiment, administration of the celecoxib derivatives is effective to decrease the severity of the infection.

The subject is preferably a mammal, such as a domesticated farm animal (e.g., cow, horse, pig) or pet (e.g., dog, cat). More preferably, the subject is a human. Alternately or in addition, celecoxib derivatives of the invention can be administered prophylactically to a subject prior to exposure to infection by *Tuberculosis*. Prophylactic administration, also referred to as prevention, is effective to decrease the likelihood of the subsequent infection in the mammal, or decrease the severity of *Tuberculosis* infection that subsequently occurs.

Lead compounds can be validated by growth assays in broth, within M. tb-infected human macrophages and in the mouse model. The drug target will be pursued by generating rare bacterial mutants in densely grown cultures exposed to the most potent drug compound(s) and then detecting the mutant gene(s) by genome sequencing and alignment analyses. A variety of celecoxib derivatives that were prepared and tested for antibacterial (e.g., antimycobacterial) activity are shown in tables 1 and II, below.

TABLE 1

Formula I Celecoxib Derivatives

| No. | Chemical structure & molecular Weight |
|---|---|
| 2-24-1 | 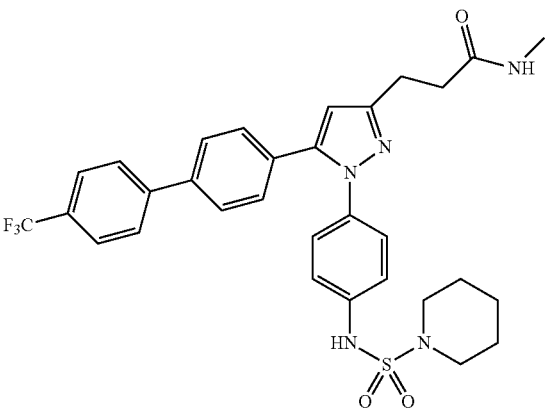 [SMILES: CNC(=O)CCc1cc(-c2ccc(-c3ccc(C(F)(F)F)cc3)cc2)n(-c2ccc(NS(=O)(=O)N3CCCCC3)cc2)n1]<br>N-methyl-3-(1-(4-(piperidine-1-sulfonamido)phenyl)-5-(4'-(trifluoromethyl)-[1,1'-biphenyl]-4-yl)-1H-pyrazol-3-yl)propanamide |
| 2-24-2 | 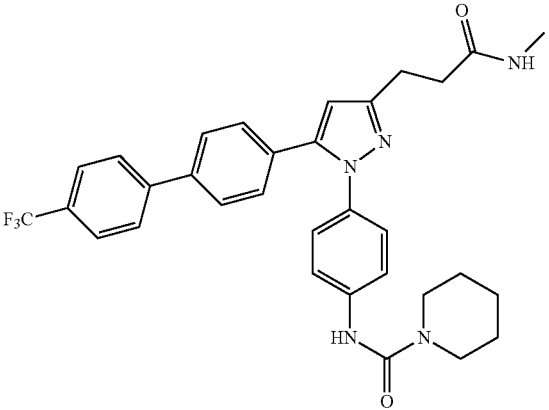 [SMILES: CNC(=O)CCc1cc(-c2ccc(-c3ccc(C(F)(F)F)cc3)cc2)n(-c2ccc(NC(=O)N3CCCCC3)cc2)n1]<br>N-(4-(3-(3-(methylamino)-3-oxopropyl)-5-(4'-(trifluoromethyl)-[1,1'-biphenyl]-4-yl)-1H-pyrazol-1-yl)phenyl)piperidine-1-carboxamide |
| 2-24-3 | 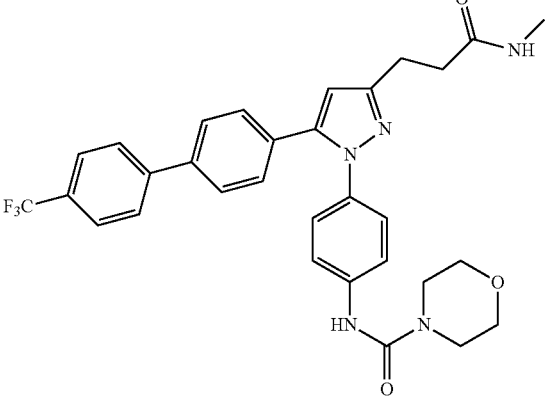<br>N-(4-(3-(3-(methylamino)-3-oxopropyl)-5-(4'-(trifluoromethyl)-[1,1'-biphenyl]-4-yl)-1H-pyrazol-1-yl)phenyl)morpholine-4-carboxamide |

TABLE 1-continued

Formula I Celecoxib Derivatives

| No. | Chemical structure & molecular Weight |
|---|---|
| 2-24-4 | 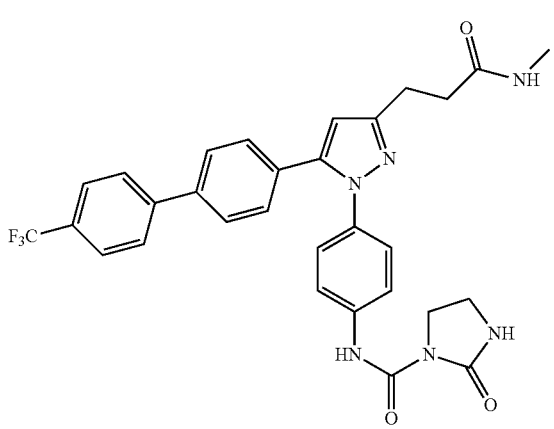 [SMILES: CNC(=O)CCc1cc(-c2ccc(-c3ccc(C(F)(F)F)cc3)cc2)n(-c2ccc(NC(=O)N3CCNC3=O)cc2)n1]<br>N-(4-(3-(3-(methylamino)-3-oxopropyl)-5-(4'-(trifluoromethyl)-[1,1'-biphenyl]-4-yl)-1H-pyrazol-1-yl)phenyl)-2-oxoimidazolidine-1-carboxamide |
| 2-24-5 | 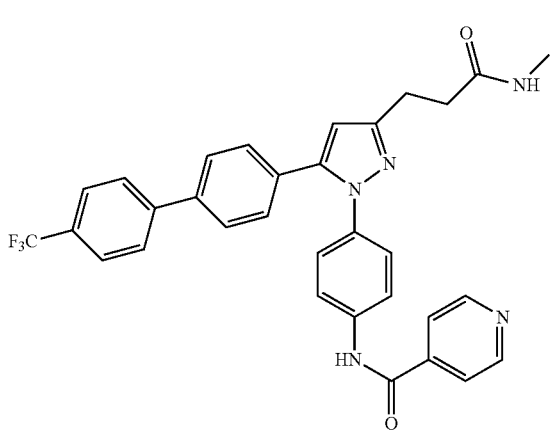 [SMILES: CNC(=O)CCc1cc(-c2ccc(-c3ccc(C(F)(F)F)cc3)cc2)n(-c2ccc(NC(=O)c3ccncc3)cc2)n1]<br>N-(4-(3-(3-(methylamino)-3-oxopropyl)-5-(4'-(trifluoromethyl)-[1,1'-biphenyl]-4-yl)-1H-pyrazol-1-yl)phenyl)isonicotinamide |
| 2-24-6 | 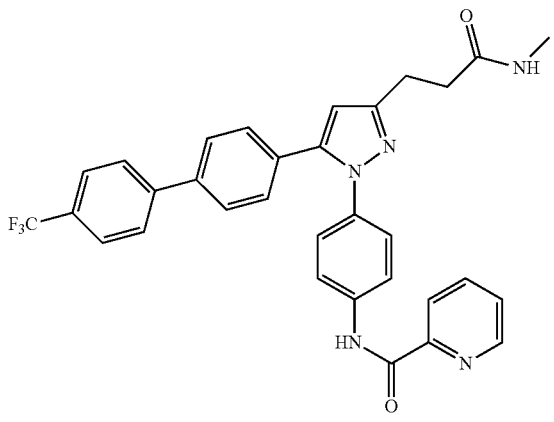<br>N-(4-(3-(3-(methylamino)-3-oxopropyl)-5-(4'-(trifluoromethyl)-[1,1'-biphenyl]-4-yl)-1H-pyrazol-1-yl)phenyl)picolinamide |

TABLE 1-continued

Formula I Celecoxib Derivatives

| No. | Chemical structure & molecular Weight |
|-----|---------------------------------------|

2-24-7

N-(4-(3-(3-(methylamino)-3-oxopropyl)-5-(4'-(trifluoromethyl)-[1,1'-biphenyl]-4-yl)-1H-pyrazol-1-yl)phenyl)nicotinamide 2-24-8

N-methyl-3-(5-(4'-(trifluoromethyl)-[1,1'-biphenyl]-4-yl)-1-(4-(3-(3-(trifluoromethyl)phenyl)ureido)phenyl)-1H-pyrazol-3-yl)propanamide 2-24-9

N-(4-(3-(3-(methylamino)-3-oxopropyl)-5-(4'-(trifluoromethyl)-[1,1'-biphenyl]-4-yl)-1H-pyrazol-1-yl)phenyl)-6-(trifluoromethyl)-nicotinamide

TABLE 1-continued

Formula I Celecoxib Derivatives

| No. | Chemical structure & molecular Weight |
|---|---|
| 2-24-10 | N-(4-(3-(3-(methylamino)-3-oxopropyl)-5-(4'-(trifluoromethy)-[1,1'-biphenyl]-4-yl)-1H-pyrazol-1-yl)phenyl)thiophene-3-carboxamide |
| 2-24-11 | 4-(dimethylamino)-N-(4-(3-(3-(methylamino)-3-oxopropyl)-5-(4'-(trifluoromethyl)-[1,1'-biphenyl]-4-yl)-1H-pyrazol-1-yl)phenyl)-benzamide |
| 2-24-12 | 4-amino-N-(4-(3-(3-(methylamino)-3-oxopropyl)-5-(4'-(trifluoromethyl)-[1,1'-biphenyl]-4-yl)-1H-pyrazol-1-yl)phenyl)-benzamide |

TABLE 1-continued

Formula I Celecoxib Derivatives

| No. | Chemical structure & molecular Weight |
|---|---|

2-24-13

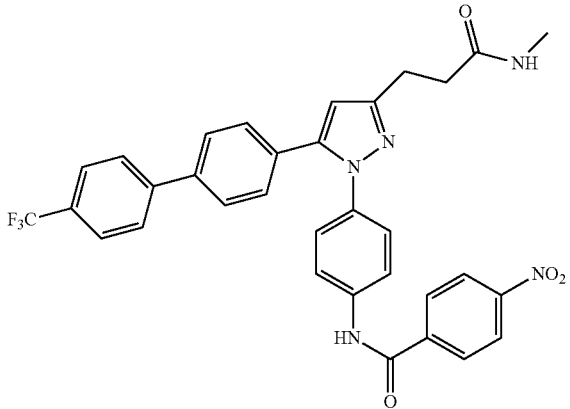 [SMILES: CNC(=O)CCc1cc(-c2ccc(-c3ccc(C(F)(F)F)cc3)cc2)n(-c2ccc(NC(=O)c3ccc(N)cc3)cc2)n1]

N-(4-(3-(3-(methylamino)-3-oxopropyl)-5-(4'-(trifluoromethyl)-[1,1'-biphenyl]-4-yl)-1H-pyrazol-1-yl)phenyl)-4-nitrobenzamide 2-24-14

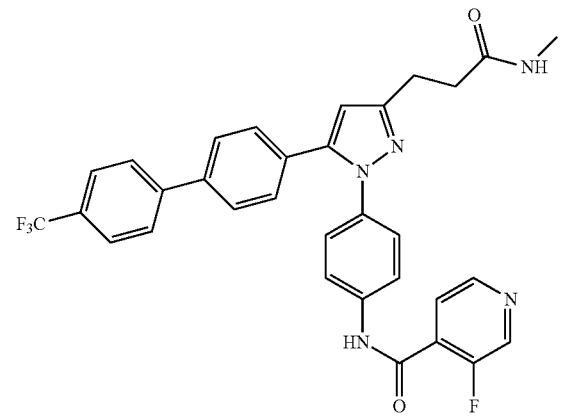

3-fluoro-N-(4-(3-(3-(methylamino)-3-oxopropyl)-5-(4'-(trifluoromethyl)-[1,1'-biphenyl]-4-yl)-1H-pyrazol-1-yl)-phenyl)isonicotinamide 2-24-15

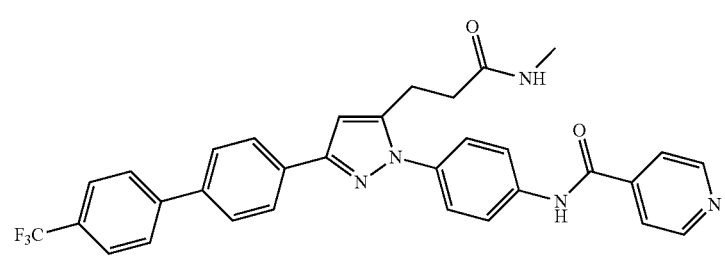 [SMILES: CNC(=O)CCc1cc(-c2ccc(-c3ccc(C(F)(F)F)cc3)cc2)nn1-c1ccc(NC(=O)c2ccncc2)cc1]

N-(4-(5-(3-(methylamino)-3-oxopropyl)-3-(4'-(trifluoromethyl)-[1,1'-biphenyl]-4-yl)-1H-pyrazol-1-yl)phenyl)-isonicotinamide TABLE 1-continued Formula I Celecoxib Derivatives

| No. | Chemical structure & molecular Weight |
|---|---|
| 2-24-16 | N-(4-(5-(phenanthren-2-yl)-3-(trifluoro-methyl)-1H-pyrazol-1-yl)phenyl)-isonicotinamide |
| 2-24-17 | 2-methyl-N-(4-(3-(3-(methylamino)-3-oxopropyl)-5-(4'-(trifluoromethyl)-[1,1'-biphenyl]-4-yl)-1H-pyrazol-1-yl)phenyl)-isonicotinamide |
| 2-24-18 | 2,3-difluoro-N-(4-(3-(3-(methylamino)-3-oxopropyl)-5-(4'-(trifluoromethyl)-[1,1'-biphenyl]-4-yl)-1H-pyrazol-1-yl)phenyl)-isonicotinamide |

TABLE 1-continued

Formula I Celecoxib Derivatives

| No. | Chemical structure & molecular Weight |
|---|---|
| 2-24-19 | 2-fluoro-N-(4-(3-(3-(methylamino)-3-oxopropyl)-5-(4'-(trifluoromethyl)-[1,1'-biphenyl]-4-yl)-1H-pyrazol-1-yl)phenyl)-isonicotinamide |
| 2-24-20 | 3-chloro-N-(4-(3-(3-(methylamino)-3-oxopropyl)-5-(4'-(trifluoromethyl)-[1,1'-biphenyl]-4-yl)-1H-pyrazol-1-yl)phenyl)-isonicotinamide |
| 2-24-21 | 2-methoxy-N-(4-(3-(3-(methylamino)-3-oxopropyl)-5-(4'-(trifluoromethyl)-[1,1'-biphenyl]-4-yl)-1H-pyrazol-1-yl)phenyl)-isonicotinamide |

TABLE 1-continued

Formula I Celecoxib Derivatives

| No. | Chemical structure & molecular Weight |
|---|---|
| 2-24-22 | N-(4-(3-(3-(methylamino)-3-oxopropyl)-5-(4'-(trifluoromethyl)-[1,1'-biphenyl]-4-yl)-1H-pyrazol-1-yl)phenyl)-2-(trifluoromethyl)isonicotinamide |
| 2-24-23 | N-(4-(3-(3-(methylamino)-3-oxopropyl)-5-(4'-(trifluoromethyl)-[1,1'-biphenyl]-4-yl)-1H-pyrazol-1-yl)phenyl)quinoline-4-carboxamide |
| 2-24-24 | 3-(1-(4-(2-(dimethylamino)acetamido)-phenyl)-5-(4'-(trifluoromethyl)-[1,1'-biphenyl]-4-yl)-1H-pyrazol-3-yl)-N-methylpropanamide |

TABLE 1-continued

Formula I Celecoxib Derivatives

| No. | Chemical structure & molecular Weight |
|---|---|
| 2-24-25 | 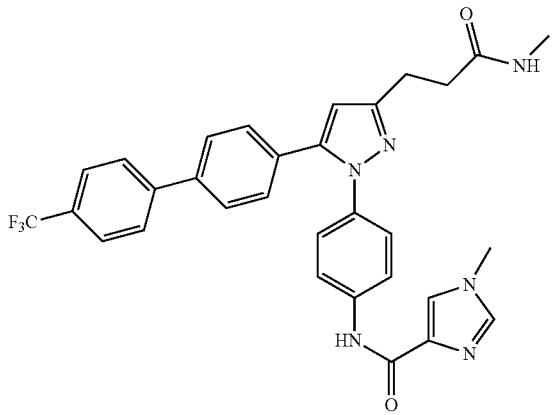 [SMILES: CNC(=O)CCc1cc(-c2ccc(-c3ccc(C(F)(F)F)cc3)cc2)n(-c2ccc(NC(=O)c3cn(C)cn3)cc2)n1] 1-methyl-N-(4-(3-(3-(methylamino)-3-oxopropyl)-5-(4'-(trifluoromethyl)-[1,1'-biphenyl]-4-yl)-1H-pyrazol-1-yl)phenyl)-1H-imidazole-4-carboxamide |
| 2-24-26 | 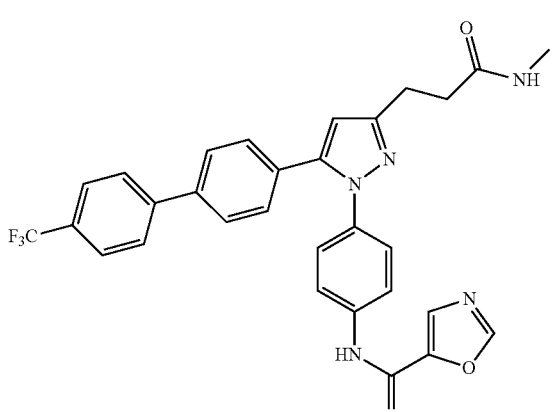 N-(4-(3-(3-(methylamino)-3-oxopropyl)-5-(4'-(trifluoromethyl)-[1,1'-biphenyl]-4-yl)-1H-pyrazol-1-yl)phenyl)oxazole-5-carboxamide |
| 2-24-27 | 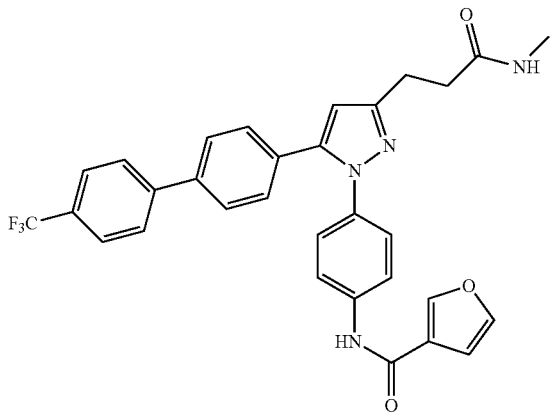 [SMILES: CNC(=O)CCc1cc(-c2ccc(-c3ccc(C(F)(F)F)cc3)cc2)n(-c2ccc(NC(=O)c3ccoc3)cc2)n1] N-(4-(3-(3-(methylamino)-3-oxopropyl)-5-(4'-(trifluoromethyl)-[1,1'-biphenyl]-4-yl)-1H-pyrazol-1-yl)phenyl)furan-3-carboxamide |

TABLE 1-continued
Formula I Celecoxib Derivatives
| No. | Chemical structure & molecular Weight |
|---|---|
| 2-24-28 | 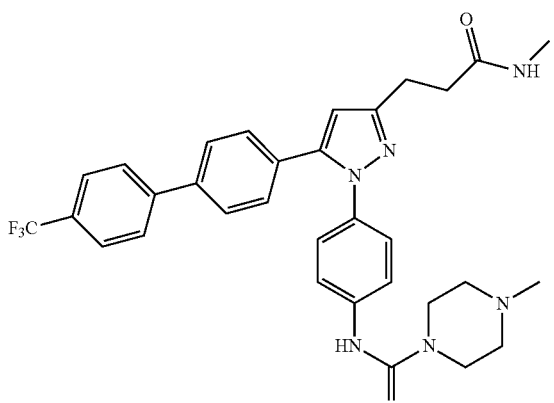<br>4-methyl-N-(4-(3-(3-(methylamino)-3-oxopropyl)-5-(4'-trifluoromethyl)-[1,1'-biphenyl]-4-yl)-1H-pyrazol-1-yl)phenyl)piperazine-1-carboxamide |
TABLE 2
Formula II Celecoxib Derivatives
| SBS-Tr-1 | 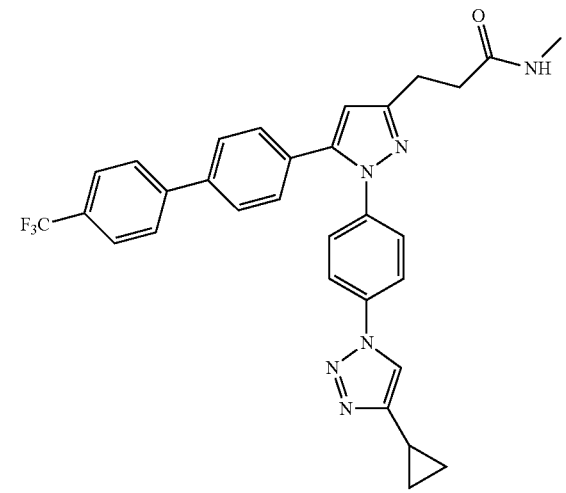 [SMILES: CNC(=O)CCc1cc(-c2ccc(-c3ccc(C(F)(F)F)cc3)cc2)n(-c2ccc(-n3cc(C4CC4)nn3)cc2)n1]<br>3-(1-(4-(4-cyclopropyl-1H-1,2,3-triazol-1-yl)phenyl)-5-(4'-(trifluoromethyl)-[1,1'-biphenyl]-4-yl)-1H-pyrazol-3-yl)-N-methylpropanamide |

TABLE 2-continued
Formula II Celecoxib Derivatives
SBS-Tr-2
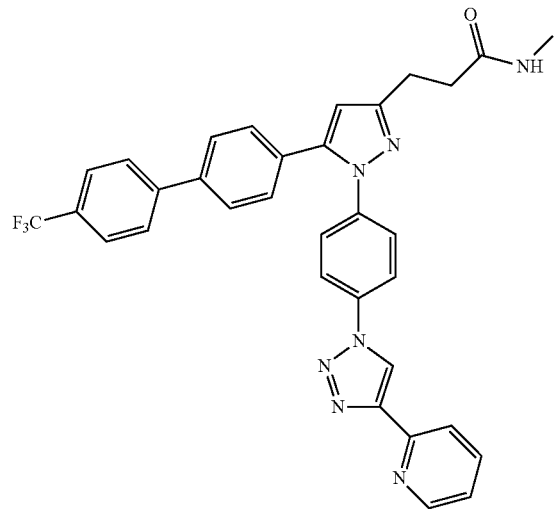 [SMILES: CNC(=O)CCc1cc(-c2ccc(-c3ccc(C(F)(F)F)cc3)cc2)n(-c2ccc(-n3cc(-c4ccccn4)nn3)cc2)n1]
N-methyl-3-(1-(4-(4-(pyridin-2-yl)-1H-1,2,3-triazol-1-yl)phenyl)-5-(4'-(trifluoromethyl)-[1,1'-biphenyl]-4-yl)-1H-pyrazol-3-yl)propanamide
SBS-Tr-3
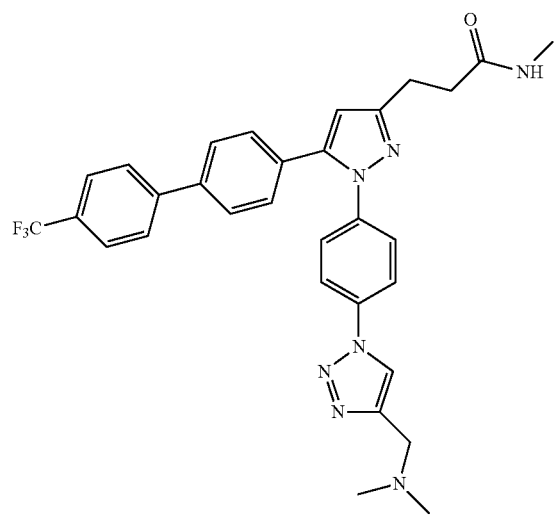 [SMILES: CNC(=O)CCc1cc(-c2ccc(-c3ccc(C(F)(F)F)cc3)cc2)n(-c2ccc(-n3cc(CN(C)C)nn3)cc2)n1]
3-(1-(4-(4-((dimethylamino)methyl)-1H-1,2,3-triazol-1-yl)phenyl)-5-(4'-(trifluoromethyl)-[1,1'-biphenyl]-4-yl)-1H-pyrazol-3-yl)-N-methylpropanamide TABLE 2-continued
Formula II Celecoxib Derivatives
SBS-Tr-4
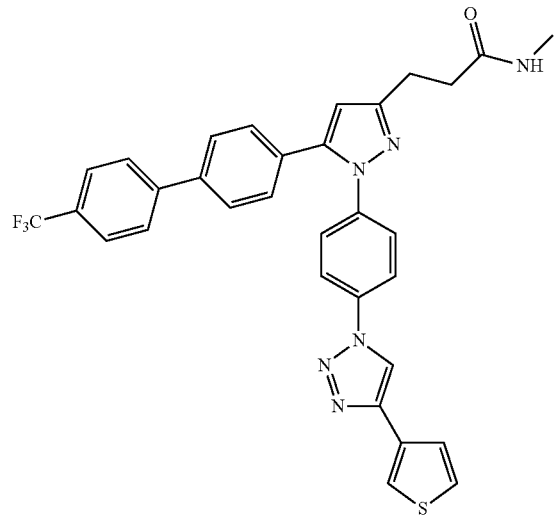 [SMILES: CNC(=O)CCc1cc(-c2ccc(-c3ccc(C(F)(F)F)cc3)cc2)n(-c2ccc(-n3cc(-c4ccsc4)nn3)cc2)n1]
N-methyl-3-(1-(4-(4-(thiophen-3-yl)-1H-1,2,3-triazol-1-yl)phenyl)-5-(4'-(trifluoromethyl)-[1,1'-biphenyl]-4-yl)-1H-pyrazol-3-yl)propanamide
SBS-Tr-5
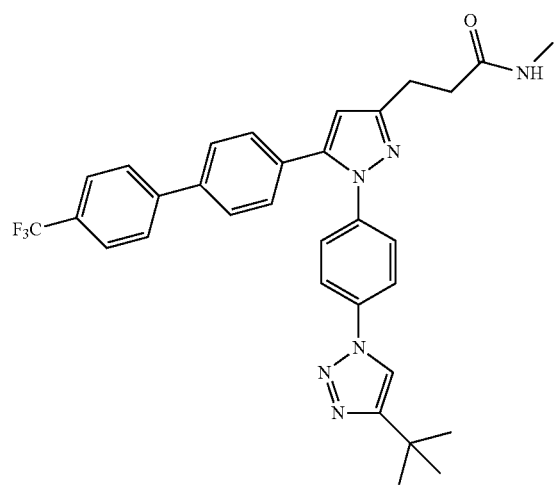 [SMILES: CNC(=O)CCc1cc(-c2ccc(-c3ccc(C(F)(F)F)cc3)cc2)n(-c2ccc(-n3cc(C(C)(C)C)nn3)cc2)n1]
3-(1-(4-(4-tert-butyl)-1H-1,2,3-triazol-1-yl)phenyl)-5-(4'-(trifluoromethyl)-[1,1'-biphenyl]-4-yl)-1H-pyrazol-3-yl)-N-methylpropanamide TABLE 2-continued
Formula II Celecoxib Derivatives
SBS-Tr-6
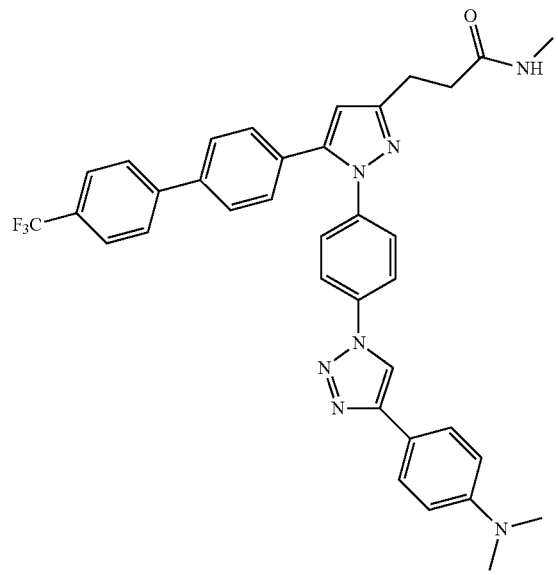 [SMILES: CNC(=O)CCc1cc(-c2ccc(-c3ccc(C(F)(F)F)cc3)cc2)n(-c2ccc(-n3cc(-c4ccc(N(C)C)cc4)nn3)cc2)n1]
3-(1-(4-(4-(4-(dimethylamino)phenyl)-1H-1,2,3-triazol-1-yl)phenyl)-5-
(4'-(trifluoromethyl)-[1,1'-biphenyl]-4-yl)-1H-pyrazol-3-yl)-N-
methylpropanamide
SBS-Tr-7
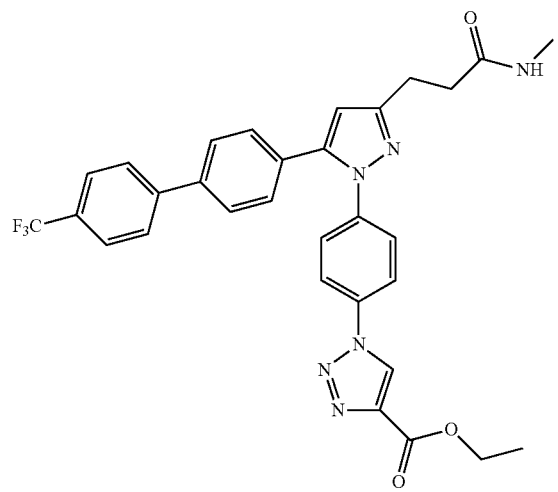 [SMILES: CCOC(=O)c1cn(-c2ccc(-n3nc(CCC(=O)NC)cc3-c3ccc(-c4ccc(C(F)(F)F)cc4)cc3)cc2)nn1]
ethyl 1-(4-(3-(3-(methylamino)-3-oxopropyl)-5-(4'-(trifluoromethyl)-
[1,1'-biphenyl]-4-yl)-1H-pyrazol-1-yl)phenyl)-1H-1,2,3-triazole-4-
carboxylate TABLE 2-continued
Formula II Celecoxib Derivatives
SBS-Tr-8
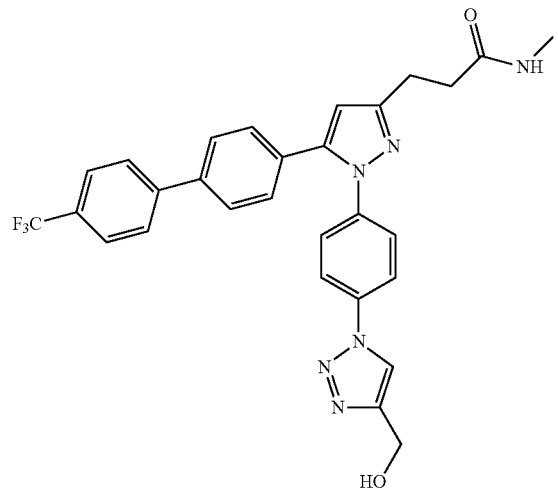 [SMILES: CNC(=O)CCc1cc(-c2ccc(-c3ccc(C(F)(F)F)cc3)cc2)n(-c2ccc(-n3cc(CO)nn3)cc2)n1]
3-(1-(4-(4-(hydroxymethyl)-1H-1,2,3-triazol-1-yl)phenyl)-5-(4'-
(trifluoromethyl)-[1,1'-biphenyl]-4-yl)-1H-pyrazol-3-yl)-N-
methylpropanamide
SBS-Tr-9
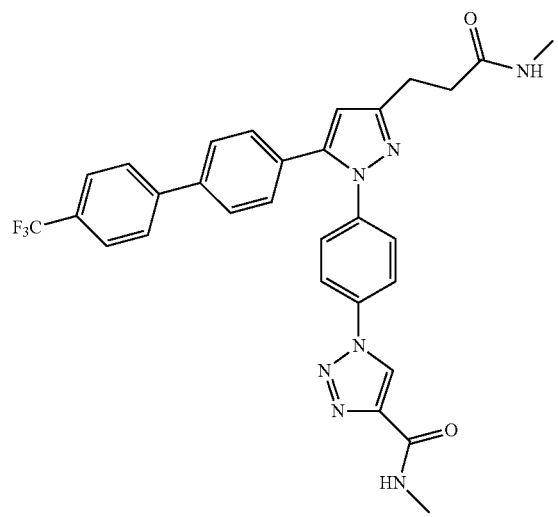 [SMILES: CNC(=O)CCc1cc(-c2ccc(-c3ccc(C(F)(F)F)cc3)cc2)n(-c2ccc(-n3cc(C(=O)NC)nn3)cc2)n1]
N-methyl-1-(4-(3-(3-(methylamino)-3-oxopropyl)-5-(4'-(trifluoromethyl)-
[1,1'-biphenyl]-4-yl)-1H-pyrazol-1-yl)phenyl)-1H-1,2,3-triazole-4-
carboxamide

TABLE 2-continued
Formula II Celecoxib Derivatives
SBS-Tr-10
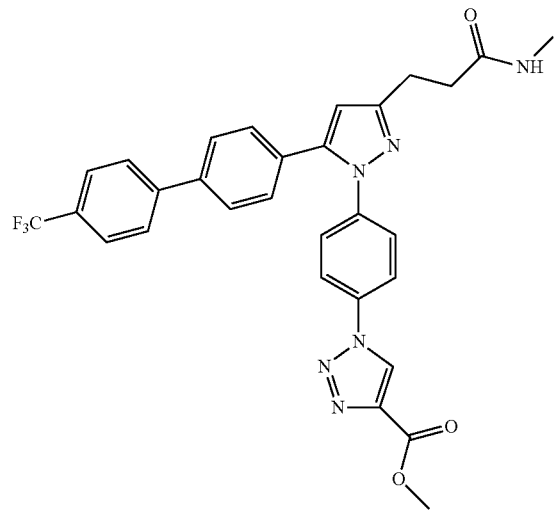 [SMILES: CNC(=O)CCc1cc(-c2ccc(-c3ccc(C(F)(F)F)cc3)cc2)n(-c2ccc(-n3cc(C(=O)OC)nn3)cc2)n1]
methyl 1-(4-(3-(3-(methylamino)-3-oxopropyl)-5-(4'-trifluoromethyl)-
[1,1'-biphenyl]-4-yl)-1H-pyrazol-1-yl)phenyl)-1H-1,2,3-triazole-4-
carboxylate
SBS-Tr-11
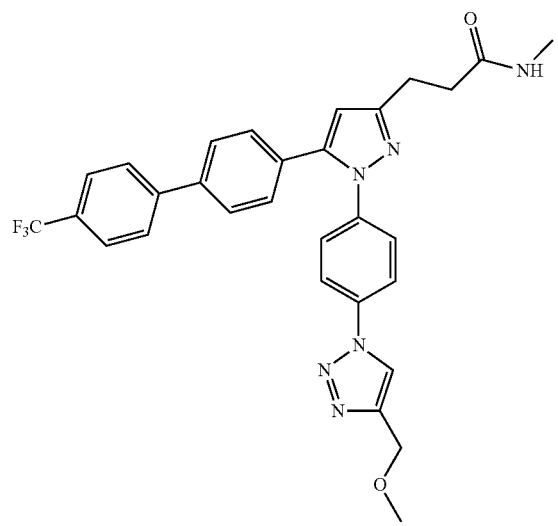 [SMILES: CNC(=O)CCc1cc(-c2ccc(-c3ccc(C(F)(F)F)cc3)cc2)n(-c2ccc(-n3cc(COC)nn3)cc2)n1]
3-(1-(4-(4-(methoxymethyl)-1H-1,2,3-triazol-1-yl)phenyl)-5-(4'-
(trifluoro-methyl)-[1,1'-biphenyl]-4-yl)-1H-pyrazol-3-yl)-N-
methylpropanamide TABLE 2-continued
Formula II Celecoxib Derivatives
SBS-Tr-12
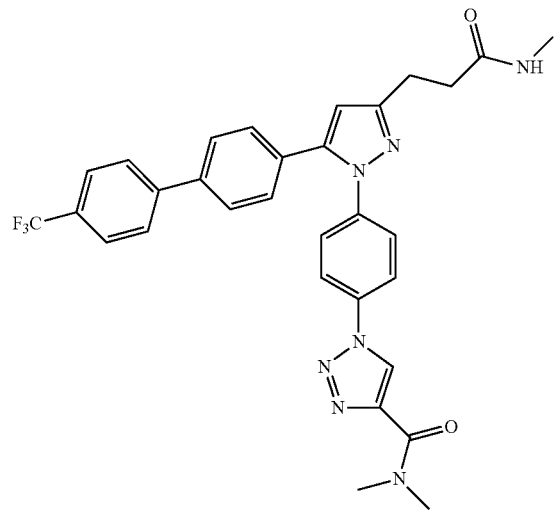 [SMILES: CNC(=O)CCc1cc(-c2ccc(-c3ccc(C(F)(F)F)cc3)cc2)n(-c2ccc(-n3cc(C(=O)N(C)C)nn3)cc2)n1]
N,N-dimethyl-1-(4-(3-(3-(methylamino)-3-oxopropyl)-5-(4'-
(trifluoromethyl)-[1,1'-biphenyl]-4-yl)-1H-pyrazol-1-yl)phenyl)-1H-
1,2,3-triazole-4-carboxamide
SBS-Tr-13
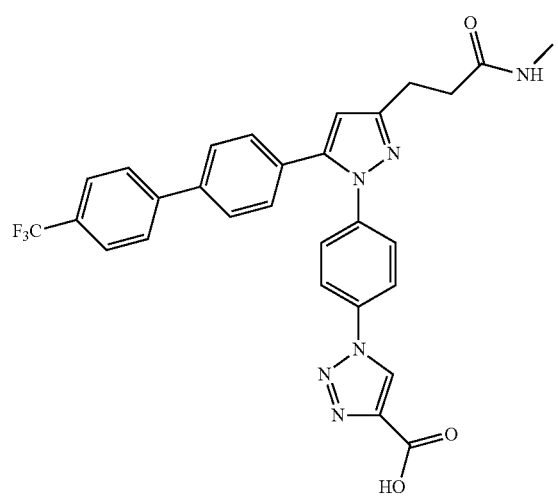 [SMILES: CNC(=O)CCc1cc(-c2ccc(-c3ccc(C(F)(F)F)cc3)cc2)n(-c2ccc(-n3cc(C(=O)O)nn3)cc2)n1]
1-(4-(3-(3-(methylamino)-3-oxopropyl)-5-(4'-(trifluoromethyl)-[1,1'-
biphenyl]-4-yl)-1H-pyrazol-1-yl)phenyl)-1H-1,2,3-triazole-4-
carboxylic acid TABLE 2-continued
Formula II Celecoxib Derivatives
SBS-Tr-14
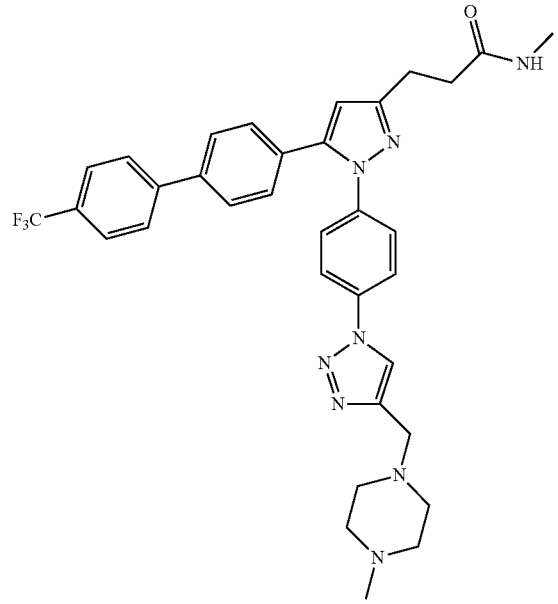 [SMILES: CNC(=O)CCc1cc(-c2ccc(-c3ccc(C(F)(F)F)cc3)cc2)n(-c2ccc(-n3cc(CN4CCN(C)CC4)nn3)cc2)n1]
N-methyl-3-(1-(4-(4-((4-methylpiperazin-1-
yl)methyl)-1H-1,2,3-triazol-1-yl)phenyl)-5-
(4'-(trifluoromethyl)-[1,1'-biphenyl]-4-yl)-
1H-pyrazol-3-yl)-propanamide
SBS-Tr-15
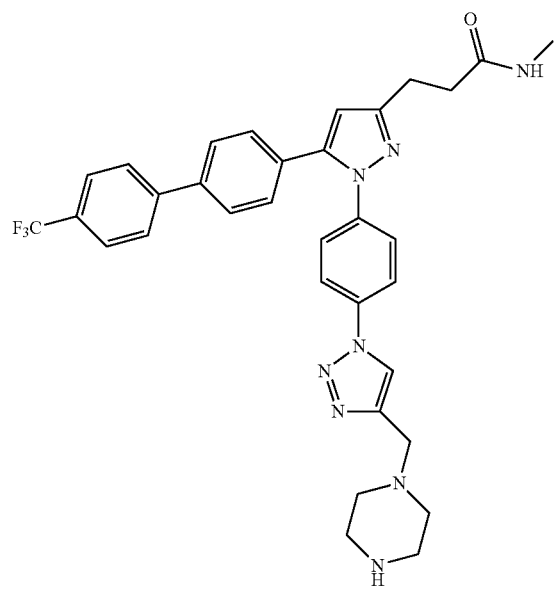 [SMILES: CNC(=O)CCc1cc(-c2ccc(-c3ccc(C(F)(F)F)cc3)cc2)n(-c2ccc(-n3cc(CN4CCNCC4)nn3)cc2)n1]
N-methyl-3-(1-(4-(4-(piperazin-1-ylmethyl)-1H-1,2,3-triazol-1-yl)
phenyl)-5-(4'-(trifluoromethyl)-[1,1'-biphenyl]-4-yl)-1H-pyrazol-3-yl)
propanamide

TABLE 2-continued
Formula II Celecoxib Derivatives
SBS-Tr-16
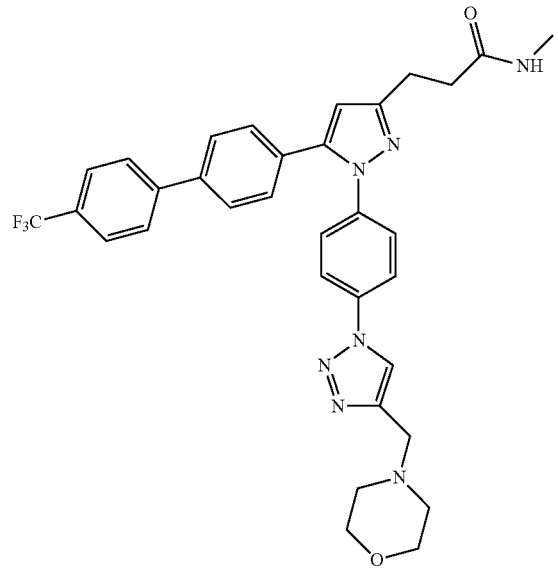 [SMILES: CNC(=O)CCc1cc(-c2ccc(-c3ccc(C(F)(F)F)cc3)cc2)n(-c2ccc(-n3cc(CN4CCOCC4)nn3)cc2)n1]
N-methyl-3-(1-(4-(4-(morpholinomethyl)-1H-1,2,3-triazol-1-yl)phenyl)-
5-(4'-(trifluoromethyl)-[1,1'-biphenyl]-4-yl)-1H-pyrazol-3-yl)
propanamide
SBS-Tr-17
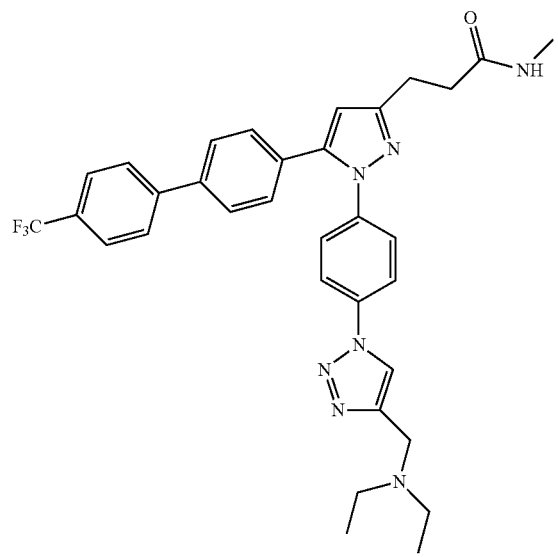 [SMILES: CCN(CC)Cc1cn(-c2ccc(-n3nc(CCC(=O)NC)cc3-c3ccc(-c4ccc(C(F)(F)F)cc4)cc3)cc2)nn1]
3-(1-(4-(4-((diethylamino)methyl)-1H-1,2,3-triazol-1-yl)phenyl)-5-(4'-
(trifluoromethyl)-[1,1'-biphenyl]-4-yl)-1H-pyrazol-3-yl)-N-
methylpropanamide TABLE 2-continued
Formula II Celecoxib Derivatives
SBS-Tr-18
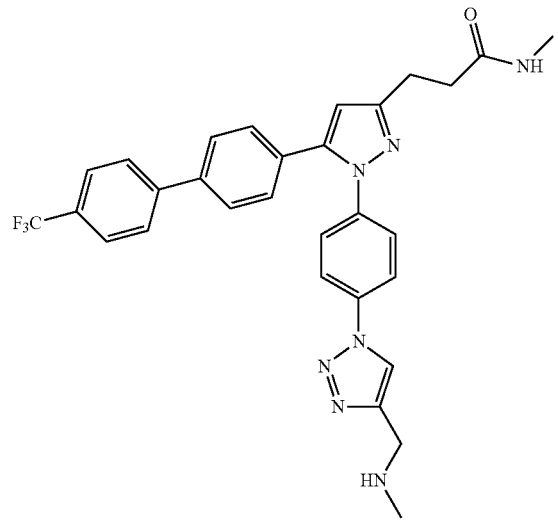
N-methyl-3-(1-(4-(4-((methylamino)methyl)-1H-1,2,3-triazol-1-yl)phenyl)-5-(4'-(trifluoromethyl)-[1,1'-biphenyl]-4-yl)-1H-pyrazol-3-yl)propanamide
SBS-Tr-19
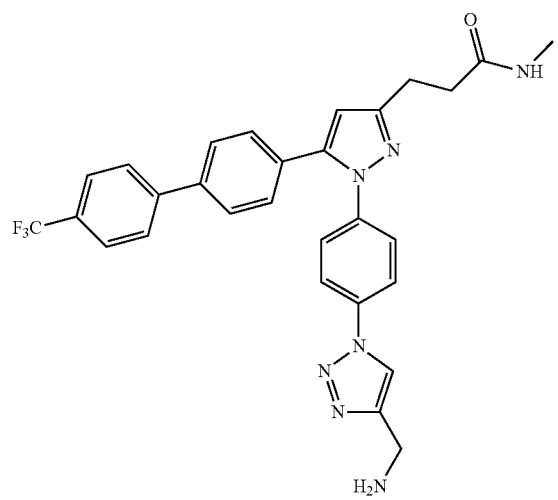 [SMILES: CNC(=O)CCc1cc(-c2ccc(-c3ccc(C(F)(F)F)cc3)cc2)n(-c2ccc(-n3cc(CN)nn3)cc2)n1]
3-(1-(4-(4-(aminomethyl)-1H-1,2,3-triazol-1-yl)phenyl)-5-(4'-(trifluoromethyl)-[1,1'-biphenyl]-4-yl)-1H-pyrazol-3-yl)-N-methylpropanamide TABLE 2-continued
Formula II Celecoxib Derivatives
SBS-Tr-20
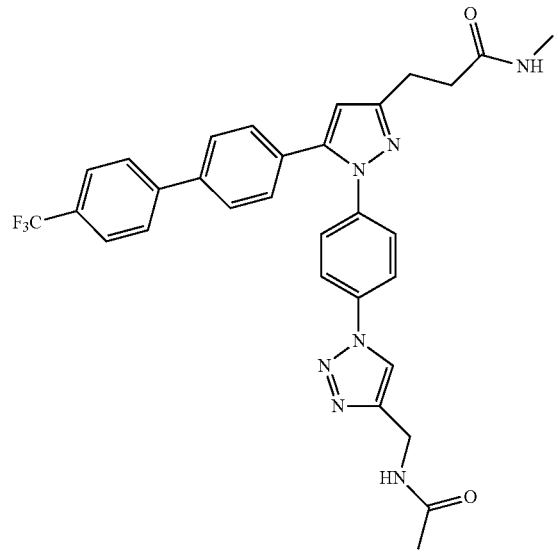 [SMILES: CNC(=O)CCc1cc(-c2ccc(-c3ccc(C(F)(F)F)cc3)cc2)n(-c2ccc(-n3cc(CNC(C)=O)nn3)cc2)n1]
3-(1-(4-(4-(acetamidomethyl)-1H-1,2,3-triazol-1-yl)phenyl)-5-(4'-
(trifluoromethyl)-[1,1'-biphenyl]-4-yl)-1H-pyrazol-3-yl)-N-
methylpropanamide
SBS-Tr-21
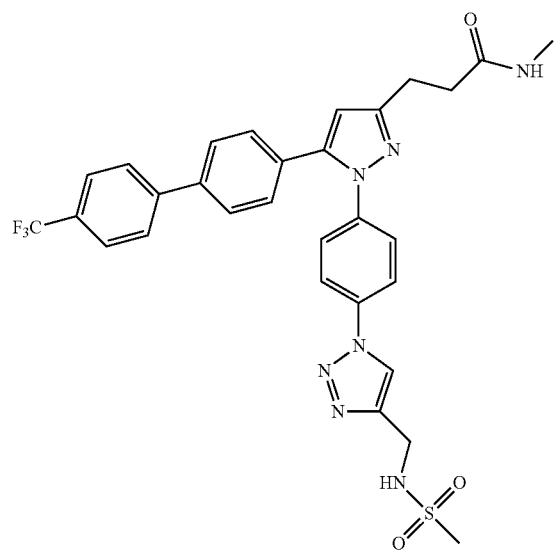 [SMILES: CNC(=O)CCc1cc(-c2ccc(-c3ccc(C(F)(F)F)cc3)cc2)n(-c2ccc(-n3cc(CNS(C)(=O)=O)nn3)cc2)n1]
N-methyl-3-(1-(4-(4-(methylsulfonamidomethyl)-1H-1,2,3-triazol-1-yl)
phenyl)-5-(4'-(trifluoromethyl)-[1,1'-biphenyl]-4-yl)-1H-pyrazol-3-yl)
propanamide TABLE 2-continued Formula II Celecoxib Derivatives SBS-Tr-22

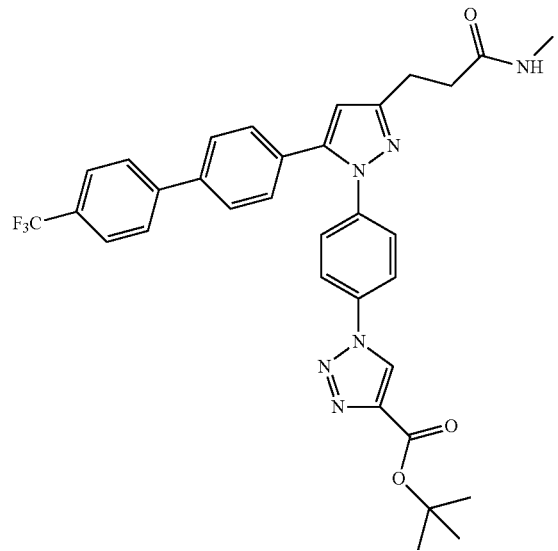 [SMILES: CNC(=O)CCc1cc(-c2ccc(-c3ccc(C(F)(F)F)cc3)cc2)n(-c2ccc(-n3cc(C(=O)OC(C)(C)C)nn3)cc2)n1]

tert-butyl 1-(4-(3-(3-(methylamino)-3-oxopropyl)-5-(4'-
(trifluoromethyl)-[1,1'-biphenyl]-4-yl)-1H-pyrazol-1-yl)phenyl)-1H-1,2,3-
triazole-4-carboxylate SBS-Tr-23

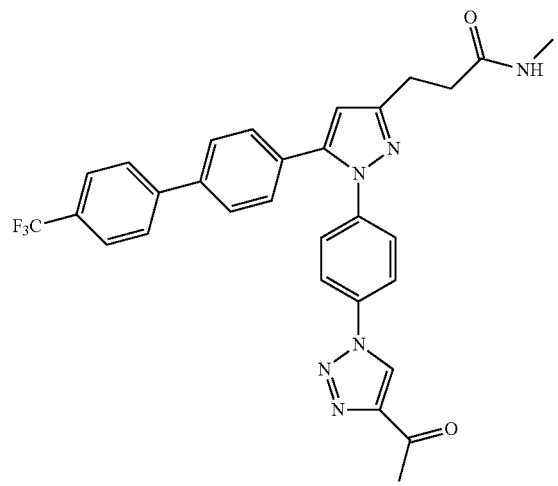 [SMILES: CNC(=O)CCc1cc(-c2ccc(-c3ccc(C(F)(F)F)cc3)cc2)n(-c2ccc(-n3cc(C(C)=O)nn3)cc2)n1]

3-(1-(4-(4-acetyl-1H-1,2,3-triazol-1-yl)phenyl)-5-(4'-
(trifluoromethyl)-[1,1'-biphenyl]-4-yl)-1H-pyrazol-3-yl)-
N-methylpropanamide SBS-Tr-24

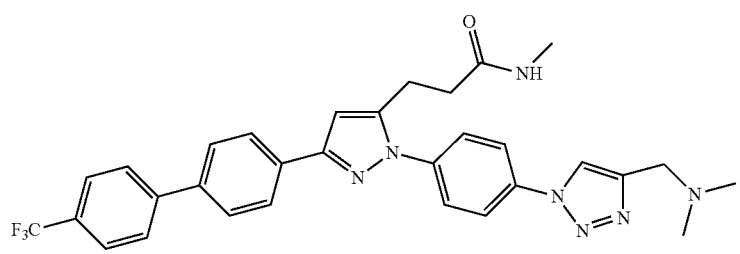 [SMILES: CNC(=O)CCc1cc(-c2ccc(-c3ccc(C(F)(F)F)cc3)cc2)nn1-c1ccc(-n2cc(CN(C)C)nn2)cc1]

3-(1-(4-(4-((dimethylamino)methyl)-1H-1,2,3-triazol-1-yl)phenyl)-3-(4'-(trifluoromethyl)-[1,1'-
biphenyl]-4-yl)-1H-pyrazol-5-yl)-N-methylpropanamide TABLE 2-continued
Formula II Celecoxib Derivatives
SBS-Tr-25
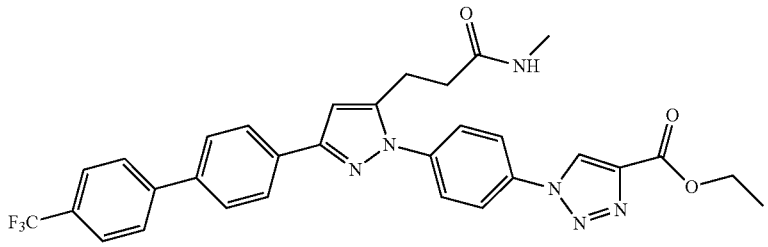 [SMILES: CCOC(=O)c1cn(-c2ccc(-n3nc(-c4ccc(-c5ccc(C(F)(F)F)cc5)cc4)cc3CCC(=O)NC)cc2)nn1]
ethyl 1-(4-(5-(3-(methylamino)-3-oxopropyl)-3-(4'-(trifluoromethyl)-[1,1'-biphenyl]-4-yl)-1H-
pyrazol-1-yl)phenyl)-1H-1,2,3-triazole-4-carboxylate
SBS-Tr-26
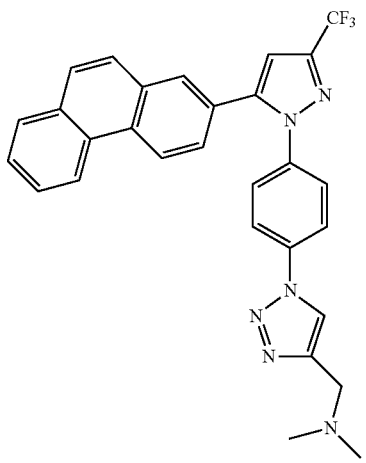 [SMILES: CN(C)Cc1cn(-c2ccc(-n3nc(C(F)(F)F)cc3-c3ccc4c(ccc5ccccc54)c3)cc2)nn1]
N,N-dimethyl-1-(1-(4-(5-(phenanthren-2-
yl)-3-(trifluoromethyl)-1H-pyrazol-1-
yl)phenyl)-1H-1,2,3-triazol-4-
yl)methanamine
SBS-Tr-27
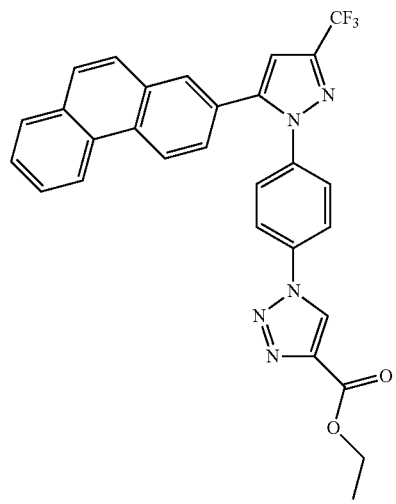 [SMILES: CCOC(=O)c1cn(-c2ccc(-n3nc(C(F)(F)F)cc3-c3ccc4c(ccc5ccccc54)c3)cc2)nn1]
ethyl 1-(4-(5-(phenanthren-2-yl)-3-
(trifluoromethyl)-1H-pyrazol-1-yl)phenyl)-1H-
1,2,3-triazole-4-carboxylate

TABLE 2-continued

Formula II Celecoxib Derivatives

SBS-Tr-28

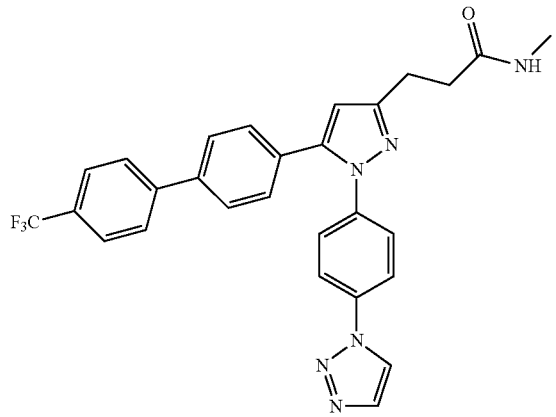 [SMILES: CNC(=O)CCc1cc(-c2ccc(-c3ccc(C(F)(F)F)cc3)cc2)n(-c2ccc(-n3ccnn3)cc2)n1]

3-(1-(4-(1H-1,2,3-triazol-1-yl)phenyl)-5-(4'-(trifluoromethyl)-[1,1'-biphenyl]-4-yl)-1H-pyrazol-3-yl)-N-methylpropanamide Administration and Formulation of Celecoxib Derivatives The present invention also provides pharmaceutical compositions that include celecoxib derivatives such as those defined by formula I or formula II as an active ingredient, and a pharmaceutically acceptable liquid or solid carrier or carriers, in combination with the active ingredient. Any of the compounds described above as being suitable for the treatment of *Tuberculosis* can be included in pharmaceutical compositions of the invention.

The celecoxib derivatives can be administered as pharmaceutically acceptable salts. Pharmaceutically acceptable salt refers to the relatively non-toxic, inorganic and organic acid addition salts of the celecoxib derivatives. These salts can be prepared in situ during the final isolation and purification of the celecoxib derivative, or by separately reacting a purified celecoxib derivative with a suitable counterion, depending on the nature of the celecoxib derivative, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more celecoxib derivatives together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The celecoxib derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, parental (including subcutaneous, intramuscular, intraperitoneal, and intravenous), and pulmonary (e.g., by inhalation or insufflation therapy using, e.g., via an aerosol, e.g., through the mouth or nose) administration.

Formulations of the present invention suitable for oral administration may be presented as discrete units such as tablets, troches, capsules, lozenges, wafers, or cachets, each containing a predetermined amount of the active agent as a powder or granules, as liposomes containing the celecoxib derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of celecoxib derivative (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Anti-Mycobacterial Activity of Celecoxib Derivatives

The anti-mycobacterial activity of parent compound OSU-03012 and its four derivatives, cpd-2, cpd-J, cpd-9 and cpd-20, was tested against *M. smegmatis* and M. tb. These derivatives have previously shown anti-bacterial properties for some other bacterial pathogens. In a colony-forming unit (CFU) assay to determine bacterial survival, the derivative compound cpd-2 was shown to significantly kill both *M. smegmatis* and T. tb compared to the parent OSU-03012 and the other derivatives. See FIG. 1. The structures of cpd-2, cpd-J, cpd-9, and cpd-20 are shown in table 3, below:

TABLE 3

Initial test compounds

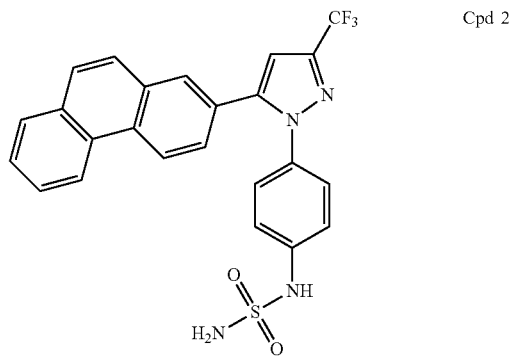

TABLE 3-continued

Initial test compounds

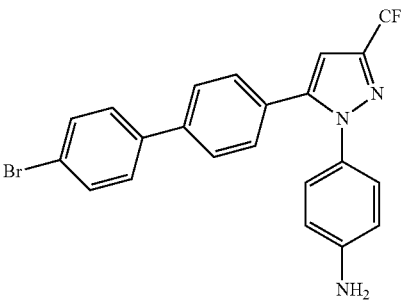

Cpd 20

Thirty six derivatives of cpd-2 (designated cpd2 1-36) were then synthesized. In order to screen a larger number of compounds, the inventors developed a bioluminescence-based method by constructing a luciferase-expressing reporter M. tb strain which contains the entire Lux operon cloned in a mycobacterial integrative expression vector.

Use of this bioluminescent strain does not require the addition of luciferase substrate in the screening assay. Screening of 36 compounds by this method yielded four candidates with activity (cpd2-21, cpd2-24, cpd-21, and cpd2-31); cpd2-25 being capable of killing M. tb nearly as effectively as the anti-TB drug isoniazid (INH) at concentrations down to 2.5 μg/ml over a 48 h period (FIG. 2). In addition, the decreased toxicity and inhibition of intramacrophage growth are shown in FIGS. 3*a* and 3*b*.

By using the bioluminesce assay, the combined effect of each of the four most active compounds was tested with INH to determine any possible synergy between the lead compound and the known TB drug. Compound cpd2-25, but showed a significant effect on M. tb killing when combined with INH at 2.5 μg/ml.

Another set of 28 derivatives of cpd-2-24 (designated cpd2-24-1 through cpd2-24-28) were prepared. See Table 1. Upon screening, four compounds (cpd2-24-3, cpd2-24-5, cpd2-24-6, and cpd2-24-7) were identified as being particularly effective. See FIGS. 4*a* and 4*b*. In addition, the in vitro antimycobacterial activity of triazole-based derivative compounds SBS-Tr-1 through SBS-Tr-28 (shown in Table 2) at 5 μM concentration against M. tb during 72 h time period. See FIGS. 5*a* and 5*b*. Further tests were conducted to evaluate addition derivatives of both types, as shown in FIGS. 6-7.

An experiment was performed to test inhibitory versus bactericidal properties of these derivative compounds on M. tb growth within human macrophages, the host cell niche, to establish the intracellular growth profile of M. tb in the presence of increasing concentrations of the known anti-TB drug INH by using the bioluminescence assay. Because of the lower multiplicity of infection (MOI) and, hence, the lower number of intracellular replicating bacilli, the infected-macrophage lysate produced significantly less RLUs compared to the in vitro assay. Nonetheless, the experiment makes it clear that we will be successful in establishing a workable bioluminescence method for screening test drugs against M. tb inside macrophages.

Based on an analysis of the active structures, the inventors have determined that there is a preference for an extended amide side chain on the C3-position of the pyrazole ring and a bulky aromatic system however, with a high degree of flexibility in the size of the substituent on the N atom of the aniline structure.

Construction of a luciferase-expressing *M. smegmatis* reporter strain. The inventors have developed an M. tb reporter strain for the bioluminescence assay of drug compounds, which is described in Example 3. In a similar way, a *M. smegmatis* reporter strain will be created. *smegmatis* competent cells will be electroporated with pMV306hsp+ Lux plasmid DNA (obtained from Brian Robertson, Imperial College, UK) and selected on kanamycin-containing 7H11 agar plate. This expression plasmid construct contains the entire Lux operon. The recombinant reporter clone will be confirmed by PCR using the Lux gene-specific primers and the luciferase expression will be confirmed by reading the bioluminescence emitted by the reporter clone.

CFU assay. Reporter strains of *M. smegmatis* and M. tb will be grown in broth to their mid-log phases. A portion of the culture will be washed with a re-suspended in complete 7H9 medium. Designated concentrations of control (INH) and test drugs will be added to the culture in a 14-ml snap-capped polypropylene tube (BD Bioscience) and incubated at 37° C. with shaking for up to 72 h. At different points (4, 24, 48 or 72 h), a portion of the treated culture will be serially diluted with 7H9 broth and plated on 7H11 agar media for incubation at 37° C. After several days of growth (~4-6 days for *M. smegmatis* and ~14-16 days for M. tb), colonies will be counted for CFU per ml culture Bioluminescence and CFU assays for intra-macrophage M. tb against test compounds. Human MOMs will be isolated from the blood of healthy human donors using our lab-established method 17 suspensions of M. tb bacilli will be prepared as described previously. Twelve-day old human MDM monolayers will be infected with M. tb (Lux) reporter strain with an MOT of 1:1 for 2 h. Monolayers will be washed, repleted with low-serum-containing medium, and then exposed to designated concentrations of control (INH) and test drugs for up to 72 hours at 37° C. Infected macrophages will be lysed at different time points (4, 24, 48 and 72 h) according to our protocol. A portion of the lysates at each time point will be read by a luminometer and the read-out values expressed in RLUs, while another portion of the lysates will be diluted with 7H9 broth for CFU counts as described above. Another aim is to examine the effect of 1-2 lead compounds on the pathogenesis of M. tb infection in the aerosol mouse model.

Methodology for Dosing Studies:

TB Infection:

In addition to MDR TB, a drug-susceptible strain (*M. tuberculosis* Erdman strain) will be used for comparison. Balb/C mice (n=5 per group/performed twice) will be anesthetized with an i.p. injection of ketamine/xylazine. Aerosolized TB generated by using the Glas-col inhalation device will deliver 5-100 CFUs to the lung in OSU's CDC-approved BSL3 facility using trained personnel. Throughout the study, mice will be sacrificed if they are clearly moribund and show evidence of debilitating disease such as self-induced isolation, unthrifty appearance (rough hair coat, hunched appearance), decreased activity levels, malaise, or excessive weight loss.

Organ Bacterial Load:

At 0, 14, 21, 100 days post infection the lungs, spleen, and livers will be removed, homogenized, serially diluted onto 7H11 agar plates, and CFUs counted after 21 days.

Routes of Dosing Evaluation:

3 drug administration routes at 3 dosages will be evaluated for treatment after TB infection. Balb/C mice (n=5, performed twice) will be used in this study. Organ bacterial load will be evaluated at day 25 post infection. i.v. and i.p. compound treatment studies: Compounds will be re-suspended in approximately 200 μL of PBS and injected in the tail vein (i.v.) or intraperitoneal cavity (i.p) with a sterile syringe. Compound treatment will follow the same drug administration as has been shown to decrease M. tb CFUs in organs 5-fold. Jagannath et al., Nat. Med. 15, 267-276 (2009). Compounds will be administered at 10 days post exposure for of 30 days, administered once a day. i.p. compound treatment studies: Compounds will be re-suspended in approximately 50 μL of PBS and 25 μL will be added to each nare. Compounds will be administered at 10 days post exposure for 30 days, once a day.

Methodology for Histology Studies

Balb/C mice (n=5, performed twice) will be monitored for histopathologic response (e.g. granuloma formation) after infection with M. tb and treatment with PBS, compounds or INH/Rifampin for drug susceptible TB and thioridazine HCL for MDR TB as used previously. Treatment will be administered 10 days post exposure and given once a day for 30 days at the optimum dose and route established above. INH/Rifampin or Thioridazine HCL will be given as a positive control at 0.5 mg/day/kg i.p. beginning at the same treatment time frame and continuing for 30 days, given twice a day. Blood samples before infection and post mortem will be evaluated for cytokines (e.g. IL-12p40, IFN-γ, TNF-α, IL-10, IL-4).

Methodology for Bacterial Load Studies

Balb/C mice (n=5, performed twice), as outlined above, will be infected with M. tb and organ bacterial load counted at 1, 14, 21, and 100 days post infection. Treatment will be administered as above. At specified time points, organs from Balb/C mice (n=5, performed twice) will be formalin-fixed and stained with H&E for granuloma formation with Ziehi-Neelsen to detect acid-fast bacilli. The goal of this is to help illustrate the ability of the identified compounds to treat a drug susceptible and MDR strain of M. tb.

Example 2

Synthesis of Example Test Compounds

Figure 8:
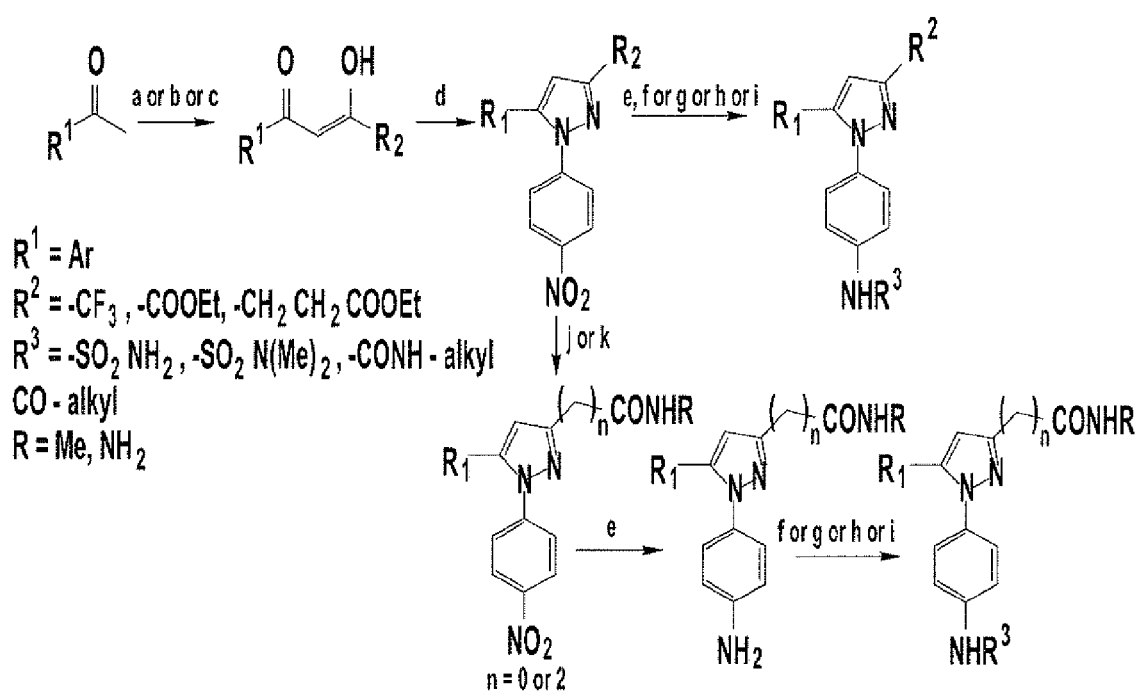
FIG. 8 provides a scheme showing the steps in the synthesis of the basic structure of the Celecoxib derivatives described herein.

An overview of the synthesis of the backbone structure for various test compounds is shown in FIG. 8.

Reagents and reaction conditions: (a) ethyl trifluoroacetate, NaH, THF; (b) diethyloxalate, NaOEt, EtOH; (c) ethyl 4-(1H-benzo[d][1,2,3]triazol-1-yl)-4-oxobutanoate, MgBr.O($C_2H_5$), $CH_2Cl_2$, DIPEA; (d) (4-nitrophenyl)hydrazine hydrochloride, TsOH, EtOH, microwave 130° C.; (e) $H_2$, 10% Pd/C, MeOH/EtOAc, 35 psi; (f) chlorosulfonyl isocyanate, t-BuOH, THF, pyridine then 20% TFA in $CH_2Cl_2$, rt; (g) alkyl isocyanate, pyridine, DMAP, THF, rt; (h) N,N-dimethylsulfonyl chloride, pyridine, DMAP, THF, rt; (i) alkylchloride, pyridine, DMAP, THF, rt; (j) 2 M $MeNH_2$ in EtOH or $NH_2NH_2$ in Sealed tube, reflux.

Step a. To a suspension of ethyl trifluoroacetate (1.2 mmol) and NaH (1.25 mmol) in anhydrous THF, individual ketone substrates (1 mmol) in anhydrous THF were slowly added at 25° C. The resulting mixture was stirred for 5 h, concentrated, diluted with ethyl acetate, washed, in tandem, with water, 1N HCl and brine. The organic phase was dried, filtered and concentrated. The residue was purified by flash column chromatography to afford pure 1,3-diketones in 45-68% yields.

Step b. To an ice cold EtOH (25 mL), Na (1.15 mmol) was added portion wise. The suspension was stirred at rt for 30 min to get clear solution. The appropriate acetophenones (1 mmol) was added followed by addition of diethyloxalate (1.1 mmol). The resulting mixture was stirred at rt for 2-5 h. The reaction mixture was carefully acidify using 2N HCl. The precipitate was collected by filtration, washed with water and dried to give desired 1,3-diketones in 75-88% yields.

Example compounds are (Z)-Methyl 4-(anthracen-9-yl)-2-hydroxy-4-oxobut-2-enoate and (Z)-3-Hydroxy-1-(4'-(trifluoromethyl)-[1,1'-biphenyl]-4-yl)pent-2-en-1-one.

Step c, To the appropriate acetophenones (1 mmol) in dry methylene chloride (25 mL) was added ethyl 4-(1H-benzo [d][1,2,3]triazol-1-yl)-4-oxobutanoate (1.5 mmol) and magnesium bromide diethyl etherate (2 mmol/g) under argon. The resulting solution was stirred under argon for 10 min, added dropwise N,N-diisopropylethylamine (2 mmol), stirred for 16 h, and washed, in tandem, with 10% HCl (50 mL) and water (20 mL). The organic phase was dried and concentrated. The residue was purified by chromatography (ethyl acetate/hexane), followed by recrystallization in ethanol to furnish 1,3-diketones in 40-75% yields.

Example compounds are (Z)-Ethyl 4-hydroxy-6-oxo-6-(4'-(trifluoromethyl)-[1,1'-biphenyl]-4-yl)hex-4-enoate and (Z)-Ethyl 6-(anthracen-9-yl)-4-hydroxy-6-oxohex-4-enoate.

Step d. To a solution of 1,3-diketones (2.5 mmol) in ethanol (10 mL) was added 4-nitro-phenylhydrazine hydrochloride (3 mmol) and 4-methylbenzene-sulfonic acid (2.5 mmol). The resulting solution was stirred under microwave at 120° C. for 10 min, concentrated, and recrystallized from ethanol to obtain pyrazoles in 80-90% yields.

Example compounds are 1-(4-Nitrophenyl)-3-(trifluoromethyl)-5-(4'-(trifluoromethyl)-[1,1'-biphenyl]-4-yl)-18-pyrazole; Ethyl 1-(4-nitrophenyl)-5-(4'-(trifluoromethyl)-[1,1'-biphenyl]-4-yl)-1H-pyrazole-3-carboxylate; Ethyl 5-(anthracen-9-yl)-1-(4-nitrophenyl)-1H-pyrazole-3-carboxylate; Ethyl 3-(5-(anthracen-9-yl)-1-(4-nitrophenyl)-1H-pyrazol-3-yl)propanoate; and Ethyl 3-(1-(4-nitrophenyl)-5-(4'-(trifluoromethyl)-[1,1'-biphenyl]-4-yl)-1H-pyrazol-3-yl) propanoate.

Step e. To a solution of an appropriate nitro-intermediate (1 mmol) in methanol/ethyl acetate (1:3, 50 mL) was added Pd on activated charcoal (15 mg). The resulting mixture was stirred under $H_2$(g) at 45 psi for 12 h, filtered, and concentrated. The residue was then purified by chromatography to give the corresponding amino derivatives in 85-91% yields.

Example compounds are Ethyl 1-(4-aminophenyl)-5-(anthracen-9-yl)-1H-pyrazole-3-carboxylate; 4-(3-(Trifluoromethyl)-5-(4'-(trifluoromethyl)-[1,1'-biphenyl]-4-yl)-1H-pyrazol-1-yl)aniline; 3-(1-(4-Aminophenyl)-5-(4'-(trifluoromethyl)-[1,1'-biphenyl]-4-yl)-1H-pyrazol-3-yl)-N-methylpropanamide; and 3-(1-(4-Aminophenyl)-5-(anthracen-9-yl)-1H-pyrazol-3-yl)-N-methylpropanamide.

Step f. Chlorosulfonyl isocyanate (1.1 mmol) was added dropwise to an ice-cold solution of t-BuOH (1.2 mmol) in dry THF, which was then added to a mixture of appropriate amino derivatives (1 mmol), generated from step e, and pyridine (2 mmol) in THF. The reaction mixture was stirred at 25° C. for 3 h, and concentrated. The residue was treated with 20% trifluoroacetic acid in $CH_2Cl_2$ for 3 h, washed with 10% $NaHCO_3$, dried, and concentrated. The residue was purified by flash column chromatograph to give desired sulfonamide derivatives in 70-75% yields.

Example compounds include N-[4-(5-p-Tolyl-3-trifluoromethyl-pyrazol-1-yl)-phenyl]-amino sulfonamide; N-[4-(5-Biphenyl-4-yl-3-trifluoromethyl-pyrazol-1-yl)-phenyl]-aminosulfonamide; N-{4-[5-(4'-Methylbiphenyl-4-yl)-3-trifluoromethyl-pyrazol-1-yl]-phenyl}-amino sulfonamide; N-{4-[5-(4'-Bromobiphenyl-4-yl)-3-trifluoromethyl-pyrazol-1-yl]-phenyl}-aminosulfonamide; N-[4-(5-Naphthalen-2-yl-3-trifluoromethyl-pyrazol-1-yl)-phenyl]-aminosulfonamide; N-[4-(5-Anthracen-9-yl-3-trifluoromethyl-pyrazol-1-yl)-phenyl]-aminosulfonamide; N-[4-(5-Anthracen-2-yl-3-trifluoromethyl-pyrazol-1-yl)-phenyl]-amino sulfonamide; Ethyl 5-(anthracen-9-yl)-1-(4-(sulfamoylamino)phenyl)-1H-pyrazole-3-carboxylate; 5-(Anthracen-9-yl)-N-methyl-1-(4-(sulfamoylamino)phenyl)-1H-pyrazole-3-carboxamide; 5-Anthracen-9-yl)-N-methyl-1-(4-(sulfamoylamino)phenyl)-1H-pyrazole-3-hydrazide; N-(4-(3-(Trifluoromethyl)-5-(4'-(trifluoromethyl)-[1,1'-biphenyl]-4-yl)-18-pyrazol-1-yl)phenyl)morpholine-4-carboxamide; tert-Butyl N-(4-(3-(trifluoromethyl)-5-(4'-trifluoromethyl)-[1,1'-biphenyl]-4-yl)-18-pyrazol-1-yl)phenyl) sulfamoylcarbamate; N-Methyl-3-(1-(4-(sulfamoylaminophenyl)-5-(4'-(trifluoromethyl)-[1,1'-biphenyl]-4-yl)-1H-pyrazol-3-yl) propanamide; 3-(5-(Anthracen-9-yl)-1-(4-(sulfamoylamino) phenyl)-1H-pyrazol-3-yl)-N-methyl propanamide; and tert-Butyl N-(4-(3-(3-(methylamino)-3 oxopropyl)-5-(4'-(trifluoromethyl)-[1,1'-biphenyl]-4-yl)-1H-pyrazol-1-yl) phenyl)sulfamoylcarbamate.

Step g. Appropriate alkyl isocyanate (5 mmol) was added slowly to an ice-cold solution of appropriate amino derivatives (1 mmol), generated from step e, and pyridine (2 mmol) in dry THF. The reaction mixture was stirred at 25° C. for 2 days under argon, and concentrated. The residue was washed extracted with EA, washed with 1N HCl and the organic layer was evaporated to dryness. The residue was purified by flash column chromatograph to furnish desired urea derivatives in 40-55% yields.

Example compounds include 1-isopropyl-3-(4-(3-(trifluoromethyl)-5-(4'-(trifluoromethyl)-[1,1'-biphenyl]-4-yl)-18-pyrazol-1-yl)phenyl)urea; 3-(1-(4-(3-isopropylureido)phenyl)-5-(4'-(trifluoromethyl)-[1,1'-biphenyl]-4-yl)-18-pyrazol-3-yl)-N-methylpropanamide; 3-(1-(4-(3-(tert-Butyl)ureido)phenyl)-5-(4'-(trifluoromethyl)-[1,1'-biphenyl]-4-yl)-18-pyrazol-3-yl)-N-methylpropanamide; (R)—N-Methyl-3-(1-(4-(3-(1-phenylethyl)ureido)phenyl)-5-(4'-(trifluoromethyl)-[1,1'-biphenyl]-4-yl)-1H-pyrazol-3-yl)propanamide; and 3-(5-(Anthracen-9-yl)-1-(4-(3-isopropylureido)phenyl)-1H-pyrazol-3-yl)-N-methylpropanamide.

Step h. To an ice-cold solution of appropriate amino derivatives (1 mmol), generated from step e, and pyridine (2 mmol) in dry THF was added dropwise N,N-dimethylsulfonyl chloride (5 mmol). The reaction mixture was stirred at 25° C. for 3 days under argon, and concentrated. The residue was extracted with EA, washed with 1N HCl and the organic layer was evaporated to dryness. The residue was purified by flash column chromatograph to obtained desired sulfonamides in 48-60% yields.

Example compounds include 3-(1-(4-((N,N-Dimethylsulfamoyl)amino)phenyl)-5-(4'-(trifluoromethyl)-[1,1'-biphenyl]-4-yl)-1H-pyrazol-3-yl)-N-methylpropanamide and 3-(5-(Anthracen-9-yl)-1-(4-((N,N-dimethylsulfamoyl) amino)phenyl)-1H-pyrazol-3-yl)-N-methylpropanamide.

Step i. To an ice-cold solution of appropriate amino derivatives (1 mmol), generated from step e, and pyridine (2 mmol) in dry THF was added dropwise alkyl chloride (2 mmol). The reaction mixture was stirred at 25° C. overnight under argon, and concentrated. The residue was extracted with EA, washed with 1N HCl and the organic layer was evaporated to dryness. The residue was purified by flash column chromatograph to obtained desired amide in 50-60% yields to obtain N-(4-(3-(Trifluoromethyl)-5-(4'-(trifluoromethyl)-[1,1'-biphenyl]-4-yl)-1H-pyrazol-1-yl)phenyl) morpholine-4-carboxamide.

Step j. To a solution of nitro-derivatives (2 mmol), generated from step d, in ethanol (5 mL) was added 2M methylamine in ethanol solution (5 mL). The resulting solution was heated to 120° C. with stirring in a sealed tube for 16 h and concentrated. The product was purified by recrystallization in ethanol from 80-85% yields.

Example compounds include N-methyl-3-(1-(4-nitrophenyl)-5-(4'-(trifluoromethyl)-[1,1'-biphenyl]-4-yl)-1H-pyrazol-3-yl) propanamide and 3-(5-(Anthracen-9-yl)-1-(4-nitrophenyl)-1H-pyrazol-3-yl)-N-methyl propanamide.

Step k. To a solution of nitro-derivatives (1 mmol), generated from step d, in ethanol (25 mL) was added $NH_2NH_2$ (5 mmol). The reaction mixture was heated to reflux for overnight. The product was purified by recrystallization from ethanol in 70-90% yields.

Example 3

Screening the Compound Library for Anti-Mycobacterial Activities Against *M. tuberculosis* (M. Tb) by Using a Bacterial Bioluminescence Assay The inventors generated an M. tb reporter strain for the bioluminescence assay of drug compounds. This expression plasmid construct contains the entire Lux operon. The lux-containing M. tb reporter strain was grown in broth to its mid-log phase. A portion of the culture was washed with and re-suspended in complete 7H9 medium without Tween. The bacterial suspension was diluted (100-150×) in order to achieve a RLU reading of 40-50,000 per ml. Test drugs and/or the control (INH) at the indicted concentrations were added to this culture in a 14 ml vented, snap-capped polypropylene tube (BC Bioscience) and incubated at 37° C. with shaking for up to 72 h. A portion (0.1 ml) of the treated culture was removed in a 12×75 mm polystyrene tube (BD Bioscience) at different time points of incubation (0, 24, 48 or 72 h) and luminescence was analyzed in a single tube Sirius Luminometer (Berthhold). The read out values were expressed in relative fluorescence units (RLUs).

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the celecoxib derivatives are effective, the inventors are not bound by theories described herein. The invention is not limited to the exact details shown and described, for variations obvious to one skilled in the art will be included within the invention defined by the claims.

What is claimed is:

1. A compound of formula I:

I wherein $R^1$ is selected from —$NH_2$, —$CO_2H$, —$CO_2Me$, —$CONH_2$, —$CONHNH_2$, —$CONHMe$, —CO-piperazine, —CO-pyrrolidine, —CONH-glycine, —$CH_2CH_2CO_2Me$, —$CH_2CH_2CONH$—$C_1$-$C_4$ alkyl, —NHCO—$C_1$-$C_4$ alkyl, —$NHSO_2NH_2$, —$NHSO_2N$(Me)$_2$, —NHCONH—$C_1$-$C_4$ alkyl, —$NHCONH_2$, —$NHCO_2$—$C_1$-$C_4$ alkyl;

Ar is a substituted or unsubstituted phenyl, biphenyl, naphthalenyl, or anthracenyl group;

X is C=O or O=S=O, and $R^2$ is a substituted or unsubstituted cycloalkyl, heterocycloalkyl, aryl, or heteroaryl group, or a pharmaceutically acceptable salt thereof.

2. The compound of claim 1, wherein $R^1$ is —$CH_2CH_2CONH$-Me and Ar is 4'-trifluoromethyl biphenyl.

* * * * *